(12) United States Patent
Corbeil et al.

(10) Patent No.: US 8,312,836 B2
(45) Date of Patent: Nov. 20, 2012

(54) METHOD AND APPARATUS FOR APPLICATION OF A FRESH COATING ON A MEDICAL DEVICE

(75) Inventors: Scott E. Corbeil, Litchfield, NH (US); Roger Labrecque, Londonderry, NH (US); Paul Martakos, Pelham, NH (US); Theodore Karwoski, Hollis, NH (US); Steve A. Herweck, Nashua, NH (US); Suzanne Conroy, Dracut, MA (US); Brian Sunter, Londonderry, NH (US); Edward Bromander, Tewksbury, MA (US); Georgette Henrich, Dracut, MA (US)

(73) Assignee: Atrium Medical Corporation, Hudson, NH (US)

( * ) Notice: Subject to any disclaimer, the term of this patent is extended or adjusted under 35 U.S.C. 154(b) by 1122 days.

(21) Appl. No.: 12/182,261

(22) Filed: Jul. 30, 2008

(65) Prior Publication Data
US 2009/0047414 A1     Feb. 19, 2009

Related U.S. Application Data

(63) Continuation-in-part of application No. 11/238,554, filed on Sep. 28, 2005, now Pat. No. 8,001,922.

(60) Provisional application No. 60/613,745, filed on Sep. 28, 2004, provisional application No. 60/962,502, filed on Jul. 30, 2007.

(51) Int. Cl.
*B05C 3/00* (2006.01)
*A61F 2/06* (2006.01)
*A61F 2/00* (2006.01)

(52) U.S. Cl. ........ 118/400; 118/404; 623/1.15; 424/423
(58) Field of Classification Search .................. None
See application file for complete search history.

(56) References Cited

U.S. PATENT DOCUMENTS
2,368,306 A    1/1945   Kiefer et al.
(Continued)

FOREIGN PATENT DOCUMENTS
EP    0 471 566    2/1992
(Continued)

OTHER PUBLICATIONS
Non-Final Office Action for U.S. Appl. No. 11/582,135, mailed Oct. 14, 2011.
(Continued)

*Primary Examiner* — Dah-Wei Yuan
*Assistant Examiner* — Binu Thomas
(74) *Attorney, Agent, or Firm* — Morse, Barnes-Brown & Pendleton, P.C.; Sean D. Detweiler, Esq.

(57) ABSTRACT

A method, a kit, and an apparatus provide a coating on an implantable medical device. The apparatus includes housing, a sealed reservoir chamber disposed in the housing, a reducing template, and a reservoir access port. The sealed reservoir contains the coating material. The reducing template is sized to receive a medical device therethrough for application of the coating material. A seal breaching mechanism can be provided and adapted to breach the sealed reservoir upon activation of the apparatus. The reservoir access port, which is disposed in the housing, is adapted to fluidly couple the reducing template with the reservoir chamber upon activation of the apparatus for coating the medical device.

45 Claims, 17 Drawing Sheets

U.S. PATENT DOCUMENTS

| | | |
|---|---|---|
| 2,986,540 A | 5/1961 | Posnansky |
| 3,464,413 A | 9/1969 | Goldfarb et al. |
| 3,556,294 A | 1/1971 | Walck et al. |
| 3,567,820 A | 3/1971 | Sperti |
| 3,967,728 A | 7/1976 | Gordon et al. |
| 4,308,120 A | 12/1981 | Pennewiss et al. |
| 4,323,547 A | 4/1982 | Knust et al. |
| 4,557,925 A | 12/1985 | Lindahl et al. |
| 4,664,114 A | 5/1987 | Ghodstain |
| 4,813,210 A | 3/1989 | Masuda et al. |
| 4,814,329 A | 3/1989 | Harsanyi et al. |
| 4,847,301 A | 7/1989 | Murray |
| 4,880,455 A | 11/1989 | Blank |
| 4,883,667 A * | 11/1989 | Eckenhoff ................ 424/438 |
| 4,886,787 A | 12/1989 | De Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,941,308 A | 7/1990 | Grabenkort et al. |
| 4,952,419 A | 8/1990 | De Leon et al. |
| 4,968,302 A | 11/1990 | Schluter et al. |
| 5,017,229 A | 5/1991 | Burns et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,176,956 A | 1/1993 | Jevne et al. |
| 5,179,174 A | 1/1993 | Elton |
| 5,254,105 A | 10/1993 | Haaga |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,447,940 A | 9/1995 | Harvey et al. |
| 5,464,650 A | 11/1995 | Berg et al. |
| 5,480,653 A | 1/1996 | Aguadisch et al. |
| 5,509,899 A | 4/1996 | Fan et al. |
| 5,579,149 A | 11/1996 | Moret et al. |
| 5,580,923 A | 12/1996 | Yeung et al. |
| 5,591,230 A | 1/1997 | Horn et al. |
| 5,593,441 A | 1/1997 | Lichtenstein et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,736,152 A | 4/1998 | Dunn |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A | 1/2000 | Exsted et al. |
| 6,015,844 A | 1/2000 | Harvey et al. |
| 6,028,164 A | 2/2000 | Loomis |
| 6,040,330 A | 3/2000 | Hausheer et al. |
| 6,056,970 A | 5/2000 | Greenawalt et al. |
| 6,077,698 A | 6/2000 | Swan et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,811 B1 | 6/2001 | Horrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,491,938 B2 | 12/2002 | Kunz |
| 6,500,453 B2 | 12/2002 | Brey et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,323,189 B2 | 1/2008 | Pathak |
| 7,415,811 B2 * | 8/2008 | Gottlieb et al. .............. 53/425 |
| 8,124,127 B2 | 2/2012 | Faucher et al. |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |

| | | |
|---|---|---|
| 2002/0007209 A1 | 1/2002 | Scheerder et al. |
| 2002/0012741 A1 | 1/2002 | Heinz et al. |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhondt et al. |
| 2006/0036311 A1 | 2/2006 | Nakayama et al. |
| 2006/0058881 A1 | 3/2006 | Trieu |
| 2006/0067974 A1* | 3/2006 | Labrecque et al. ........ 424/426 |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0202149 A1 | 8/2007 | Faucher et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0206305 A1 | 8/2008 | Herweck et al. |
| 2008/0279929 A1 | 11/2008 | Devane et al. |
| 2009/0011116 A1 | 1/2009 | Herweck et al. |
| 2009/0181937 A1 | 7/2009 | Faucher et al. |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |

FOREIGN PATENT DOCUMENTS

| | | |
|---|---|---|
| EP | 0610731 | 8/1994 |
| EP | 0623354 B1 | 11/1994 |
| EP | 0730864 B1 | 9/1996 |
| EP | 0790822 B1 | 8/1997 |
| EP | 0873133 B1 | 10/1998 |
| EP | 0917561 B1 | 5/1999 |
| EP | 1140243 B1 | 10/2001 |
| EP | 1181943 A1 | 2/2002 |
| EP | 1270024 A1 | 1/2003 |
| EP | 1273314 A1 | 1/2003 |
| EP | 1364628 A1 | 11/2003 |
| EP | 1520795 | 4/2005 |
| EP | 1557183 A1 | 7/2005 |
| EP | 1 402 906 | 6/2011 |
| WO | WO 86/00912 | 7/1984 |
| WO | WO-90/01969 A1 | 3/1990 |
| WO | WO-95/26715 A2 | 10/1995 |
| WO | WO-97/02042 A1 | 1/1997 |
| WO | WO-97/09367 A1 | 3/1997 |
| WO | WO-97/13528 A1 | 4/1997 |
| WO | WO-98/30206 A1 | 7/1998 |
| WO | WO-98/54275 A3 | 12/1998 |
| WO | WO 99/25336 | 5/1999 |
| WO | WO-00/40278 A1 | 7/2000 |
| WO | WO-00/62830 A2 | 10/2000 |
| WO | WO-01/24866 A1 | 4/2001 |
| WO | WO-01/26585 A1 | 4/2001 |
| WO | WO 01/37808 | 5/2001 |
| WO | WO 01/60586 | 8/2001 |
| WO | WO-01/66036 A2 | 9/2001 |
| WO | WO-01/76649 A1 | 10/2001 |
| WO | WO-02/49535 A2 | 6/2002 |
| WO | WO-02/100455 A2 | 12/2002 |
| WO | WO-03/000308 A1 | 1/2003 |
| WO | WO-03/015748 A2 | 2/2003 |

| | | |
|---|---|---|
| WO | WO-03/028622 A2 | 4/2003 |
| WO | WO-03/037397 A2 | 5/2003 |
| WO | WO-03/037398 A2 | 5/2003 |
| WO | WO-03/039612 A1 | 5/2003 |
| WO | WO-03/041756 A1 | 5/2003 |
| WO | WO-03/070125 A1 | 8/2003 |
| WO | 03/092779 A1 | 11/2003 |
| WO | WO-03/092741 A1 | 11/2003 |
| WO | WO-2004/004598 A2 | 1/2004 |
| WO | WO-2004/006976 A1 | 1/2004 |
| WO | WO-2004/006978 A1 | 1/2004 |
| WO | WO 2004/028583 | 4/2004 |
| WO | WO2004091684 * | 10/2004 |
| WO | WO-2005/000165 A1 | 1/2005 |
| WO | WO-2005/016400 A1 | 2/2005 |
| WO | WO-2005/053767 A1 | 6/2005 |
| WO | WO 2005/073091 | 8/2005 |
| WO | WO 2005/116118 | 12/2005 |
| WO | 2006/024488 A2 | 3/2006 |
| WO | WO2006024488 * | 3/2006 |
| WO | WO 2006/036967 | 4/2006 |
| WO | WO 2006/102374 | 9/2006 |
| WO | WO 2007/047028 | 4/2007 |
| WO | WO 2008/057328 | 5/2008 |

OTHER PUBLICATIONS

Crivello et al., "Epoxidized triglycerides as renewable monomers in photoinitiated cationic polymerization," Chem. Mater, 1992:692-699.
Timir-Balizsy et al., "Chemical Principals of Textile Conservation," Oxford: Elsevier Science Ltd., 1998:117-119.
Supplementary European Search Report in Application No. EP 05 80 4291, dated Jul. 26, 2011.
Supplementary European Search Report for Application No. EP 05 80 2894, dated Jul. 27, 2011.
Supplementary European Search Report in Application No. EP 05 85 8430, dated Aug. 18, 2011.
Supplementary European Search Report in Application No. 05 800 844, dated Aug. 19, 2011.
Non-final Office Action for U.S. Appl. No. 11/525,390 (listed on SB/08 as US 2007/0071798), mailed Jul. 11, 2011.
Final Office Action for U.S. Appl. No. 11/237,420 (listed on SB/08 as US 2006/0078586), mailed Jul. 13, 2011.
Final Office Action for U.S. Appl. No. 12/075,223 (listed on SB/08 as US 2008/0206305), mailed Aug. 11, 2011.
Non-Final Office Action for U.S. Appl. No. 11/701,799 (listed on SB/08 as US 2008/0109017), mailed Aug. 17, 2011.
"cure" in Academic Press Dictionary of Science and Technology (1992).
"polymerization" Merriam-Webster Online Dictionary, retrieved from <www.merriam-webster.com> on Dec. 13, 2009; Merriam-Webster's Inc. 2009; pp. 1.
Ahuja, et al. Journal of Indian Pediatric Surgery 2002 7:15-20.
Autosuture, "ParietexTM Composite OS Series Mesh," retrieved online at http://www.autosuture.com/AutoSuture/pagebuilder. aspx?topicID=135734&breadcrumbs=135601:0 (2007).
Binder et al., "Chromatographic Analysis of Seed Oils, Fatty Acid Composition of Castor Oil," The Journal of the American Oil Chemists' Society, vol. 39:513-517 (1962).
CECW-EE, "Ch. 4: Coating Types and Characteristics," Engineering and Design—Painting: New Construction and Maintenance, pp. 4-1 to 4-24 (1995).
De Scheerder, Ivan K., et al. "Biocompatibility of polymer-coated oversized metallic stents implanted in normal porcine coronary arteries," Atherosclerosis, vol. 114:105-114.
Guler, et al. "Some empirical equations for oxopolymerization of linseed oil," Progress in Organic Coatings, vol. 51:365-371 (2004).
Jonasson, Lena, et al., "Cyclosporon A inhibits smooth muscle proliferation in the vascular response to injury," Proc. Natl. Acad. Sci. USA, vol. 85: 2303-2306 (1988).
Mallegol, et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Ogunniyi, D.S., "Castor oil: A vital industrial raw material," Biosource Technology, vol. 97: 1086-1091 (2006).
Redman, L.V., et al., "The drying rate of raw paint oils—a comparison," The Journal of Industrial and Engineering Chemistry, vol. 5: 630-636 (1913).
Rutkow, Ira M., et al., "Tension-free' inguinal herniorrhaphy: A preliminary report on the 'mesh plug' technique," Surgery, vol. 114:3-8 (1993).
Shahidi, Fereidoon ed.; "Bailey's Industrial Oil and Fats Products" 2005; John Wiley and Sons; vol. 5, Edible Oil and Fat Products: Processing Technologies, pp. 1-15.
Van der Giessen, Willem J., et al, "Marked Inflammatory Sequelae to Implantation of Biodegradable and Nonbiodegradable Polymers in Porcine Coronary Arteries," Circulation, vol. 94:1690-1697 (1996).
Websters Dictionary Online, Accessed on Feb. 13, 2009, entry for "polymer" p. 1 of 1.
Wikipedia, "Sirolimus," pp. 1-13, available online at http://en.wikipedia.org/wiki/Sirolimus, date accessed May 11, 2011.
Encylopedia Britannica Online, "Surface Coating", available online at http://www.britannica.com/EBchecked/topic/575029/surface-coating>, date accessed Jun. 17, 2011.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Non-final Office Action for U.S. Appl. No. 11/236,908 (listed on SB/08 as US 2006/0067974), mailed Mar. 25, 2006.
Final Office Action for U.S. Appl. No. 11/236,908 (listed on SB/08 as US 2006/0067974), mailed May 17, 2011.
Non-final Office Action for U.S. Appl. No. 11/236,908 (listed on SB/08 as US 2006/0067974), mailed Aug. 24, 2009.
Final Office Action for U.S. Appl. No. 11/236,943 (listed on SB/08 as US 2006/0067975), mailed Dec. 23, 2009.

Non-Final Office Action for U.S. Appl. No. 11/236,943 (listed on SB/08 as US 2006/0067975), mailed Mar. 5, 2009.
Non-final Office Action for U.S. Appl. No. 11/236,977 (listed on SB/08 as US 2006/0088596), mailed Aug. 3, 2009.
Final Office Action for U.S. Appl. No. 11/237,263 (listed on SB/08 as US 2006/0110457), mailed Jul. 7, 2010.
Non-final Office Action for U.S. Appl. No. 11/237,263 (listed on SB/08 as US 2006/0110457), mailed Oct. 7, 2009.
Final Office Action for U.S. Appl. No. 11/237,264 (listed on SB/08 as US 2006/0067983), mailed Jun. 2, 2010.
Non-final Office Action for U.S. Appl. No. 11/237,264 (listed on SB/08 as US 2006/0067983), mailed Oct. 5, 2009.
Final Office Action for U.S. Appl. No. 11/701,799 (listed on SB/08 as US 2008/0109017), mailed Nov. 23, 2010.
Non-final Office Action for U.S. Appl. No. 11/237,420 (listed on SB/08 as US 2006/0078586), mailed Mar. 5, 2009.
Final Office Action for U.S. Appl. No. 11/237,420 (listed on SB/08 as US 2006/0078586), mailed Nov. 4, 2009.
Non-final Office Action for U.S. Appl. No. 11/237,420 (listed on SB/08 as US 2006/0078586), mailed Dec. 6, 2010.
Non-final Office Action for U.S. Appl. No. 11/238,532 (listed on SB/08 as US 2006/0067976), mailed Mar. 30, 2009.
Final Office Action for U.S. Appl. No. 11/238,532 (listed on SB/08 as US 2006/0067976), mailed Sep. 9, 2009.
Final Office Action for U.S. Appl. No. 11/238,554 (listed on SB/08 as US 2006/0121081), mailed May 12, 2010.
Non-final Office Action for U.S. Appl. No, 11/238,554 (listed on SB/08 as US 2006/0121081), mailed Oct. 9, 2009.
Final Office Action for U.S. Appl. No. 11/238,554 (listed on SB/08 as US 2006/0121081), mailed May 1, 2009.
Non-final Office Action for U.S. Appl. No. 11/238,554 (listed on SB/08 as US 2006/0121081), mailed Jul. 25, 2008.
Non-final Office Action for U.S. Appl. No. 11/238,564 (listed on SB/08 as US 2006/0083768), mailed Apr. 16, 2008.
Final Office Action for U.S. Appl. No. 11/238,564 (listed on SB/08 as US 2006/0083768), mailed Aug. 6, 2009.
Non-final Office Action for U.S. Appl. No. 11/239,555 (listed on SB/08 as US 2006/0067977), mailed Mar. 30, 2009.
Non-final Office Action for U.S. Appl. No. 11/525,328 (listed on SB/08 as US 2007/0084144), mailed Apr. 30, 2007.
Non-final Office Action for U.S. Appl. No. 11/525,390 (listed on SB/08 as US 2007/0071798), mailed Jul. 14, 2010.
Final Office Action for U.S. Appl. No. 11/525,390 (listed on SB/08 as US 2007/0071798), mailed Feb. 21, 2011.
Final Office Action for U.S. Appl. No. 11/582,135 (listed on SB/08 as US 2007/0202149), mailed May 12, 2011.
Non-final Office Action for U.S. Appl. No. 11/582,135 (listed on SB/08 as US 2007/0202149), mailed Nov. 9, 2010.
Non-final Office Action for U.S. Appl. No. 11/582,135 (listed on SB/08 as US 2007/0202149), mailed Jan. 6, 2010.
Non-final Office Action for U.S. Appl. No. 11/582,135 (listed on SB/08 as US 2007/0202149), mailed May 12, 2009.
Non-final Office Action for U.S. Appl. No. 11/701,799 (listed on SB/08 as US 2008/0109017), mailed Apr. 12, 2010.
Non-final Office Action for U.S. Appl. No. 11/978,840 (listed on SB/08 as US 2008/0118550), mailed Dec. 3, 2010.
Non-final Office Action for U.S. Appl. No. 11/980,155 (listed on SB/08 as US 2008/0113001), mailed Mar. 24, 2011.
Non-final Office Action for U.S. Appl. No. 12/075,223 (listed on SB/08 as US 2008/0206305), mailed Dec. 8, 2010.
Non-final Office Action for U.S. Appl. No. 12/325,546 (listed on SB/08 as US 2009/0181937), mailed Feb. 25, 2010.
Final Office Action for U.S. Appl. No. 12/325,546 (listed on SB/08 as US 2009/0181937), mailed Aug. 31, 2010.
Non-final Office Action for U.S. Appl. No. 12/364,763 (listed on SB/08 as US 2009/0208552), mailed Dec. 11, 2009.
Final Office Action for U.S. Appl. No. 12/364,763 (listed on SB/08 as US 2009/0208552), mailed Sep. 21, 2010.
Final Office Action for U.S. Appl. No. 11/978,840 (listed on SB/08 as US 2008/0118550), mailed Jun. 22, 2011.
Interview summary for U.S. Appl. No. 11/236,908 (listed on SB/08 as US 2006/0067974) mailed May 5, 2009.
Interview summary for U.S. Appl. No. 11/236,908 (listed on SB/08 as US 2006/0067974) mailed Dec. 2, 2010.
Interview summary for U.S. Appl. No. 11/237,420 (listed on SB/08 as US 2006/0078586) mailed May 5, 2009.
Interview summary for U.S. Appl. No. 11/582,135 (listed on SB/08 as US 2007/0202149) mailed Dec. 7, 2010.
Interview summary for U.S. Appl. No. 12/325,546 (listed on SB/08 as US 2009/0181937) mailed Dec. 2, 2010.
Interview summary for U.S. Appl. No. 12/364,763 (listed on SB/08 as US 2009/0208552) mailed Dec. 2, 2010.
International Preliminary Report on Patentability for Application No. PCT/US08/71565, dated Apr. 5, 2010.
Final Office Action for U.S. Appl. No. 11/980,155, mailed Oct. 21, 2011.
Camurus, "In our endeavors to create the unique, we start with the best. Your product."
Drummond, Calum J. et al, "Surfactant self-assembly objects as novel drug delivery vehicles," *Current Opinion in Colloid & Interface Science*, vol. 4:449-456 (2000).
Engström, Sven, "Drug Delivery from Cubic and Other Lipid-water Phases," *Lipid Technology*, vol. 2(2):42-45 (1990).
Hwang, Chao-Wei et al, "Physiological Transport Forces Govern Drug Distribution for Stent-Based Delivery," *Circulation*, vol. 104:600-605 (2001).
Li, Shengqiao, A paper entitled, "Evaluation of the Biocompatibility and Drug Delivery Capabilities of Biological Oil Based Stent Coatings," by Li, Shengqiao of the Katholieke Universiteit Leuven.
Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," *Catheterization and Cardiovascular Diagnosis*, vol. 44:267-274 (1998).
Salu, Koen J. et al, "Addition of cytochalasin D to a biocompatible oil stent coating inhibits intimal hyperplasia in a porcine coronary model," *Coronary Artery Disease*, vol. 14(8):545-555 (2003).
Scheller, Bruno et al, "Addition of Paclitaxel to Contrast Media Prevents Restenosis After Coronary Stent Implantation," *Journal of the American College of Cardiology*, vol. 42(8):1415-1420 (2003).
International Search Report for Application No. PCT/US05/34836, dated Jul. 6, 2006.
International Search Report for Application No. PCT/US08/71565, dated Nov. 10, 2008.
Final Office Action for U.S. Appl. No. 11/980,155 (listed on SB/08 as US 2008/0113001), mailed Oct. 21, 2011.
Non-Final Office Action for U.S. Appl. No. 11/236,908 (listed on SB/08 as US 2006/0067974), mailed Dec. 2, 2011.
Non-Final Office Action for U.S. Appl. No. 12/401,243 (listed on SB/08) as US 2010/0233232), mailed Jan. 5, 2012.
Non-Final Office Action for U.S. Appl. No. 12/182,165 (listed on SB/08 as US 2009/0011116), mailed Jan. 5, 2012.
Notice of Allowance for U.S. Appl. No. 11/582,135 (listed on SB/08 as US 2007/0202149), mailed Jan. 9, 2012.
Final Office Action for U.S. Appl. No. 11/980,155 (listed on SB/08 as US-2008-0113001), mailed Oct. 21, 2011.
Final Office Action for U.S. Appl. No 12/182,165 (listed on SB/08 as US 2009-0011116), mailed Apr. 6, 2012.
Final Office Action for U.S. Appl. No 12/401,243 (listed on SB/08 as US-2010-0233232), mailed Jun. 11, 2012.
Final Office Action for U.S. Appl. No. 11/701,799 (listed on SB/08 as US 2008/0109017), mailed Feb. 13, 2012.
Non-Final Office Action for U.S. Appl. No. 11/236,908 (listed on SB/08 as US-2006-0067974), mailed Dec. 2, 2011.
Non-Final Office Action for U.S. Appl. No. 12/182,165 (listed on SB/08 as US 2009-0011116), mailed Jan. 5, 2012.
Non-Final Office Action for U.S. Appl. No. 12/401,243 (listed on SB/08 as US 2010-0233232), mailed Jan. 5, 2012.
Non-Final Office Action for U.S. Appl. No. 12/581,582 (listed on SB/08 as US 2010-0183697), mailed Mar. 14, 2012.
Notice of Allowance for U.S. Appl. No. 11/236,908 (listed on SB/08 as US-2006-0067974), mailed May 11, 2012.
Notice of Allowance for U.S. Appl. No. 11/582,135 (listed on SB/08 as US 2007-0202149), mailed Jan. 9, 2012.

* cited by examiner

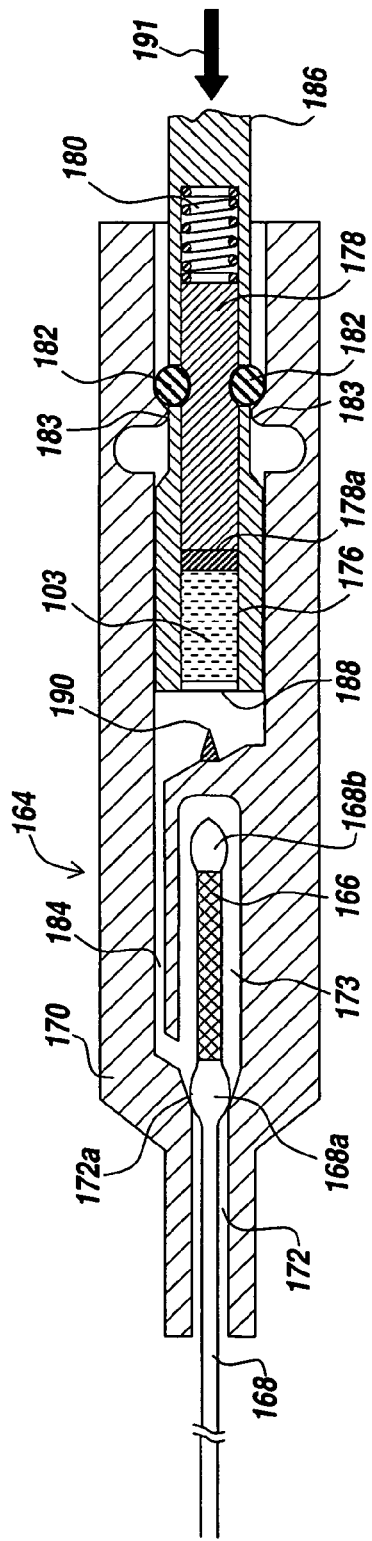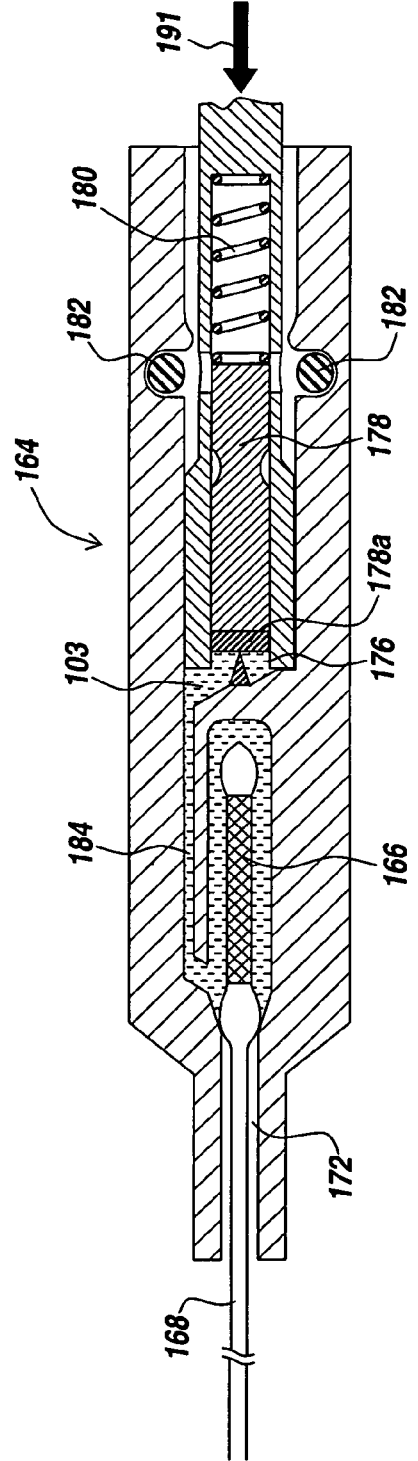
Fig. 19A
Fig. 19B

METHOD AND APPARATUS FOR APPLICATION OF A FRESH COATING ON A MEDICAL DEVICE

RELATED APPLICATIONS

The present application is a continuation-in-part of, and claims priority to and the benefit of, pending U.S. application Ser. No. 11/238,554, filed Sep. 28, 2005 which claimed priority to, and the benefit of, U.S. Provisional Application No. 60/613,745, filed Sep. 28, 2004. The present application also claims priority to and the benefit of U.S. Provisional Application No. 60/962,502, filed Jul. 30, 2007. The disclosures of said applications are hereby incorporated into the present application by reference in their entirety.

FIELD OF THE INVENTION

The present invention relates to devices and techniques for storing medical devices to be coated, and regulating coatings on those medical devices prior to use. More specifically, the present invention is directed to apparatuses and techniques for storing medical devices, such as stents, balloons, and catheters that require a coating prior to use, and providing a device or system of regulating a coating on the device prior to use. The coatings can be used for delivery of one or more biologically active agents, providing controlled short or long term release of biologically active components from the surface of the medical device, or can otherwise provide different chemical or physical characteristics to the device as coated.

BACKGROUND OF THE INVENTION

Therapeutic agents may be delivered to a targeted location in a human utilizing a number of different methods. For example, agents may be delivered nasally, transdermally, intravenously, orally, or via other conventional methods. Delivery may vary by release rate (e.g., quick release, slow release, or biphasic release). Delivery may also vary as to how the drug is administered. Specifically, a drug may be administered locally to a targeted area, or administered systemically.

With systemic administration, the therapeutic agent is administered in one of a number of different ways including orally, inhalationally, or intravenously to be systemically processed by the patient. However, there are drawbacks to systemic delivery of a therapeutic agent, one of which is that high concentrations of the therapeutic agent travel to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

An alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, minimizing or eliminating broader systemic side effects. With local delivery, the therapeutic agent that escapes the targeted tissue location dilutes as it travels to the remainder of the patient's body, substantially reducing or eliminating systemic effects.

Local delivery is often carried out using a medical device as the delivery vehicle. One example of a medical device that is used as a delivery vehicle is a stent. Boston Scientific Corporation sells the Taxus® stent, which contains a polymeric coating for delivering Paclitaxel. Johnson & Johnson, Inc. sells the Cypher® stent which includes a polymeric coating for delivery of Sirolimus.

In applying coatings to medical devices, such as stents and catheters, coverage and uniformity are important factors in getting optimal performance out of the coated medical device. If a device does not have the desired coverage then there may be areas on the device that do not have proper coating which can lead to problems. Similar problems can arise when the coating is not uniform. Non-uniform coatings can cause inconsistent interactions, especially when a therapeutic agent is being delivered. Ideally, the coating should be uniform over the desired portions of the medical device so that dosage and interaction with tissue can be better controlled.

Degradation of coating materials, and the therapeutic agents that can be included in coating materials, is a significant concern in the area of coated medical devices. Multiple strategies have been employed to prevent degradation of coating materials. An outer layer of porous biocompatible polymer covering the therapeutic coating layer has been used to control the release of the active agent and to reduce degradation of the therapeutic coating layer. The curing of coating materials by applying heat, UV light, chemical cross-linker, and/or reactive gas has also been used to reduce degradation of the coating. Unfortunately, curing a coating can reduce its therapeutic effectiveness.

In both of the aforementioned techniques, the coating material is deposited onto the medical device long before the device will be implanted into the patient. Normally, the coated device would be manufactured, packaged, and then sent to another location and stored before use. The aforementioned techniques were designed to preserve the coating material already deposited on the medical device for the long period of time between when the device is coated and when the device is implanted (typically a week to months). Preserving a coating material that is already applied to a device is difficult, in part, because the thin coating layer provides a large surface area for interaction with the surrounding environment and because oxygen, and other elements that may cause degradation, only need to diffuse a short distance through the thickness of the coating to reach all of the coating material.

A need exists for an apparatus to uniformly apply a coating material, which has been stored and optionally preserved from degradation, to a medical device shortly before the device is implanted into a patient.

SUMMARY OF THE INVENTION

In accordance with the present invention a method, an apparatus and a kit for applying a coating to a medical device, such as a stent, balloon, or catheter, shortly before implantation are provided that produce uniform consistent coverage in a repeatable and controllable manner and reduce the need for preservative components in the coating or for excessive curing or hardening of the coating.

An illustrative embodiment of the present invention includes an apparatus for coating a medical device. The apparatus includes a housing, a sealed reservoir chamber disposed in the housing, a reducing template disposed in the housing, a seal breaching mechanism disposed in the housing and a reservoir access port disposed in the housing. The reservoir chamber is adapted to contain a coating material. Additionally, the reducing template has a first end and a second end and is sized to receive the medical device through it for application of the coating material primarily at the reducing template. The seal breaching mechanism is adapted to breach the sealed reservoir chamber upon activation of the apparatus. The reservoir access port is adapted to fluidly couple the reducing template with the reservoir chamber upon activation of the apparatus for coating the medical device.

According to aspects of the present invention the reservoir chamber can form a preserving reservoir in instances where the coating material requires or benefits from preservation. Alternately, the reservoir chamber can contain a preserving reservoir. The preserving reservoir can include a sealed pod containing the coating material. The preserving reservoir can be formed of a reservoir wall comprised of a soft non-liquid layer of gelatin. The preserving reservoir can be formed of a reservoir wall comprised of a soft non-liquid layer of cellulose, for example. The preserving reservoir can be formed of a reservoir wall comprised of a soft non-liquid layer of polymeric material, elastomeric materials, bioerodable materials, glass or metal, and the like. The coating material can include a bio-absorbable liquid. The coating material can include a bio-absorbable liquid and at least one therapeutic agent. Furthermore, the coating material may not require preservation, in which case the sealed receptacle simply stores the material until it is time for use. In addition, the coating material can be a lubricating material, or can have other characteristics desirable for use with a medical device as a coating.

According to one aspect of the present invention the first end of the reducing template can be flared and can have a cross-sectional area greater than a cross-sectional area of at least a remaining portion of the reducing template. Further, according to a different aspect of the present invention, the reducing template can be sized and dimensioned to fit over the medical device providing a clearance between an inner wall of the reducing template and the medical device for receiving the coating liquid for application of the coating liquid to the medical device. In the case of the reducing template having some flexibility, elasticity, or expansion characteristics, the reducing template can stretch or expand to fit over the medical device, contacting the medical device. In such an instance a nominal clearance remains for the coating material between the medical device and the reducing template.

According to another aspect of the present invention the reservoir access port can have a first end and a second end, where the second end of the reservoir access port has at least one sharp point adapted to puncture the preserving reservoir containing coating material. Further, according to another aspect of the present invention, the aforementioned apparatus can include a plunger disposed in the housing adjacent to the reservoir chamber. This plunger can be adapted to apply a compression force to the coating material to move the coating material in the direction of the reservoir access port when depressed. According to yet another aspect of the present invention, the reservoir chamber can be disposed within a dispenser disposed in the housing.

According to one aspect of the present invention, the aforementioned apparatus can include a first seal and a second seal where the first seal seals a first end of the reducing template or the elongate lumen and the second seal seals a second end of the reducing template or the elongate lumen. The two seals can be adapted to maintain the sterile integrity of an interior of the reducing template or elongate lumen. According to another aspect of the present invention the volume of the reservoir chamber can be sized to contain a volume of coating material at least sufficient to coat one medical device. According to yet another aspect of the present invention, the housing can further include a grip.

According to other aspects of the present invention, the coating material can include an oil containing at least one form of lipid. The coating material can include an oil containing at least one form of essential fatty acid. The coating material can include a partially cured oil.

According to aspects of the present invention, the medical device can include any of a stent, a catheter and a balloon.

Another illustrative embodiment of the present invention includes a kit for coating a medical device. The kit includes a coating material, a dispenser, the medical device and instructions for use. The dispenser includes a housing, a sealed reservoir chamber containing the coating material, a reducing template disposed in the housing, a seal breaching mechanism disposed in the housing and a reservoir access port disposed in the housing. The reservoir chamber contains the coating material. The reducing template has a first end and a second end and is sized to receive the medical device through it for application of the coating material. The seal breaching mechanism is adapted to breach the sealed reservoir chamber upon activation of the apparatus. The reservoir access port is adapted to fluidly couple the reducing template with the reservoir chamber upon activation of the apparatus.

A further illustrative embodiment of the present invention is a method for using an apparatus to coat a medical device with a coating material. The method includes the steps of providing the apparatus and conveying the coating material from the reservoir chamber to the medical device through the reservoir access port. According to aspects of the illustrative embodiment, the apparatus includes a housing, a sealed reservoir chamber disposed in the housing, a reducing template disposed in the housing, a seal breaching mechanism disposed in the housing and a reservoir access port disposed in the housing. The reservoir chamber contains the coating material. The reducing template has a first end and a second end and is sized to receive the medical device through it for application of the coating material. The seal breaching mechanism is adapted to breach the sealed reservoir chamber upon activation of the apparatus. The reservoir access port is adapted to fluidly couple the reducing template with the reservoir chamber upon activation of the apparatus for coating the medical device.

According to aspects of the present invention, the method can further include inserting a dispenser containing the reservoir chamber into the housing. The method can further include the step of inserting the preserving reservoir into the reservoir chamber prior to activating the coating apparatus.

According to other aspects of the illustrative embodiment, the method can further include withdrawing the medical device from the reducing template uniformly coating the medical device. The medical device can optionally be rotated relative to the reducing template along an axis of the reducing template as the medical device is withdrawn from the reducing template.

According to aspects of the illustrative embodiment, the method can include activating the coating apparatus by releasing the coating material from the reservoir chamber. The step of activating the coating apparatus by releasing the coating material from the reservoir chamber can include the step of depressing a plunger. One of ordinary skill will appreciate that alternative mechanisms to the plunger can be utilized, including, turning a screw, turning a crank, pulling a lever, pushing a button, pulling a cord, engaging a snap fit, pressurizing with a gas, pressurizing with a fluid, depressing a reservoir, activating a spring, and the like. The step of activating the coating apparatus by releasing the coating material from the reservoir chamber can include the step of piercing a preserving reservoir containing the coating material with a portion of the reservoir access port, or alternatively removing a seal, attaching a luer fitting, attaching a connector, or bypassing a seal. The medical device can be inserted into the reducing template before the coating apparatus is activated. The medical device can be inserted into the reducing template after the coating apparatus is activated (e.g., by activating the reservoir chamber). Inserting a medical device into the reducing template can distribute coating material throughout the reducing template. In accordance with another embodiment of the present invention, the medical device can be inserted into the reducing template before the apparatus is activated and the coating is dispensed.

According to other aspects of the present invention, the method can include the step of removing sterile packaging containing the apparatus. Conveying the coating material from the reservoir chamber to the reducing template through the reservoir access port can comprise the step of applying a force to at least one wall of the reservoir chamber causing the coating material to flow toward (or in some embodiments away from) the reducing template. The step of activating the coating apparatus by releasing the coating material from the reservoir chamber can include the step of depressing a plunger. One of ordinary skill will appreciate that alternative mechanisms to the plunger can be utilized, including, turning a screw, turning a crank, pulling a lever, pushing a button, pulling a cord, engaging a snap fit, pressurizing with a gas, pressurizing with a fluid, depressing a reservoir, activating a spring, and the like. The step of activating the coating apparatus by releasing the coating material from the reservoir can include the step of piercing a preserving reservoir containing the coating material with a portion of the reservoir access port, or alternatively removing a seal, attaching a luer fitting, attaching a connector, or bypassing a seal. The method can further include the step of removing the first seal and the second seal from the reducing template or the elongate lumen.

BRIEF DESCRIPTION OF THE DRAWINGS

The aforementioned features and advantages, and other features and aspects of the present invention, will become better understood with regard to the following description and accompanying drawings, wherein:

FIG. 19A is a diagrammatic illustration of another apparatus for coating a medical device including a thumb actuated cartridge, in accordance with another embodiment of the present invention;

FIG. 19B is a diagrammatic illustration of the apparatus of FIG. 19A after the apparatus has been activated;

DETAILED DESCRIPTION

Figure 1:
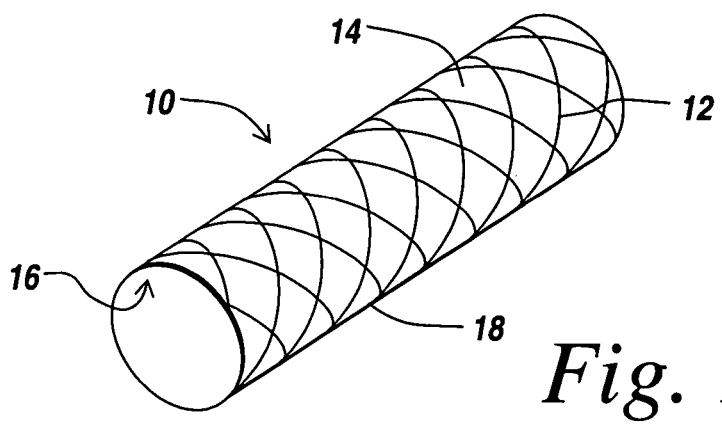
FIG. 1 is a diagrammatic illustration of a medical device, according to one embodiment of the present invention.

An illustrative embodiment of the present invention relates to the provision of a coating on an implantable medical device. An apparatus coats the medical device shortly before implantation to reduce degradation of the coating and alleviate the need for preservative components in the coating. The coating can include a bio-absorbable carrier component. In addition to the bio-absorbable carrier component, a therapeutic agent component can also be provided. However, the coating is not limited to a bio-absorbable carrier component or a therapeutic agent component. Rather, any variation of coating formed with application of a relatively liquid or fluent material that is desired for application to a medical device can be applied using the apparatus and method of the present invention. The coated medical device can be implantable in a patient to affect controlled delivery of the coating to the patient, or can be for external use.

As utilized herein, the term "bio-absorbable" generally refers to having the property or characteristic of being able to penetrate the tissue cells of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes, in a manner that does not result in cellular uptake of the biodegradable substance. Biodegradation thus relates to the breaking down and distributing of a substance through the patient's body, verses the penetration of the cells of the patient's body tissue. Biodegradable substances can cause inflammatory response due to either the parent substance or those formed during breakdown, and they may or may not be absorbed by tissues.

The phrase "controlled release" generally refers to the release of a biologically active agent in a predictable manner over the time period of weeks or months, as desired and predetermined upon formation of the biologically active agent on the medical device from which it is being released. Controlled release includes the provision of an initial burst of release upon implantation, followed by the predictable release over the aforementioned time period.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-crosslinked semi-solid. Hydrogenation can reduce or eliminate omega-3 fatty acids, and any therapeutic effects (both anti-inflammatory and wound healing) they offer.

In addition, some curing methods have been indicated to have detrimental effects on the therapeutic agent combined with the omega-3 fatty acid, making them partially or completely ineffective. Further, some heating of the omega-3 fatty acids to cure the oil can lessen the total therapeutic effectiveness of the omega-3 fatty acids, but not eliminate the therapeutic effectiveness. One characteristic that can remain after curing by certain heating methods is the non-inflammatory response of the tissue when exposed to the cured material. As such, an oil containing omega-3 fatty acids can be heated for curing purposes, and still maintain some or even a substantial portion of the therapeutic effectiveness of the omega-3 fatty acids. In addition, although the therapeutic agent combined with the omega-3 fatty acid and cured with the omega-3 fatty acid can be rendered partially ineffective, the remaining portion of the therapeutic agent can maintain pharmacological activity and in some cases be more effective than an equivalent quantity of agent delivered with other coating delivery agents. Thus, if for example, 80% of a therapeutic agent is rendered ineffective during curing, the remaining 20% of the therapeutic agent, combined with and delivered by the coating, can be efficacious in treating a medical disorder, and in some cases 20% of the therapeutic agent can have a relatively greater therapeutic effect than the same quantity of agent delivered with a polymeric or other type of coating.

For long term controlled release applications, polymers, as previously mentioned, have been utilized in combination with a therapeutic agent. Such a combination provides a platform for the controlled long term release of the therapeutic agent from a medical device. However, polymers have been determined to themselves cause inflammation in body tissue. Therefore, the polymers often must include at least one therapeutic agent that has an anti-inflammatory effect to counter the inflammation caused by the polymer delivery agent. In addition, patients that received a polymer-based implant must also follow a course of long term systemic anti-platelet therapy to offset the thrombogenic properties of the non-absorbable polymer. A significant percentage of patients that receive such implants are required to undergo additional medical procedures, such as surgeries (whether related follow-up surgery or non-related surgery) and are required to stop their anti-platelet therapy. This can lead to a thrombotic event, such as stroke, which can lead to death. Use of the bioabsorbable non-polymeric coating described herein can negate the necessity of anti-platelet therapy, and the corresponding related risks described, because there is no thrombogenic polymer reaction to the coating.

FIGS. 1 through 22, wherein like parts are designated by like reference numerals throughout, illustrate example embodiments of an apparatus and a corresponding method for coating a medical device, along with representative coated medical device examples. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 illustrates a stent 10 in accordance with one aspect of the present invention. The stent 10 is representative of a medical device that is suitable for having a coating applied thereon to affect a therapeutic result. The stent 10 is formed of a series of interconnected struts 12 having gaps 14 formed therebetween. The stent 10 is generally cylindrically shaped. Accordingly, the stent 10 maintains an interior surface 16 and an exterior surface 18.

One of ordinary skill in the art will appreciate that the illustrative stent 10 is merely exemplary of a number of different types of stents available in the industry. For example, the strut 12 structure can vary substantially. The material of the stent can also vary from a metal, such as stainless steel, Nitinol, nickel, tantalum, magnesium, and titanium alloys, to cobalt chromium alloy, ceramic, plastic, and polymer type materials. One of ordinary skill in the art will further appreciate that the present invention is not limited to use with stents. Instead, the present invention has application with a wide variety of medical devices. For purposes of clarity, the following description will refer to a stent as the exemplar medical device. The terms medical device and stent are interchangeable with regard to the applicability of the present invention. Accordingly, reference to one or another of the stent, or the medical device, is not intended to unduly limit the invention to the specific embodiment described.

Figure 2:
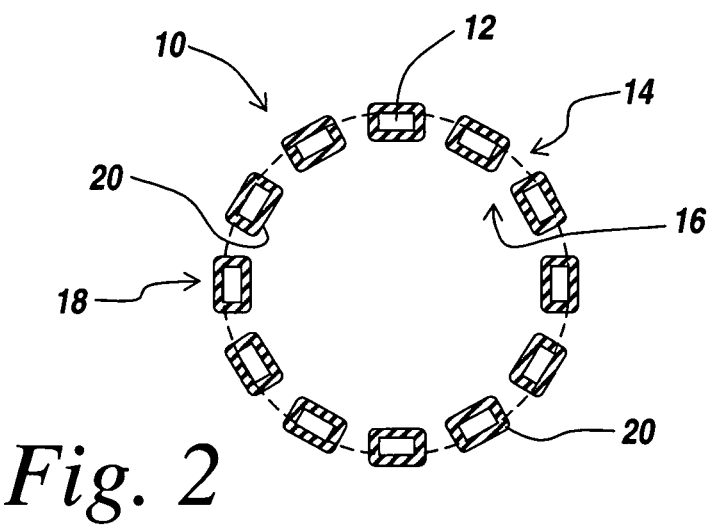
FIG. 2 is a cross-sectional view of the medical device in accordance with one aspect of the present invention.
Figure 3:
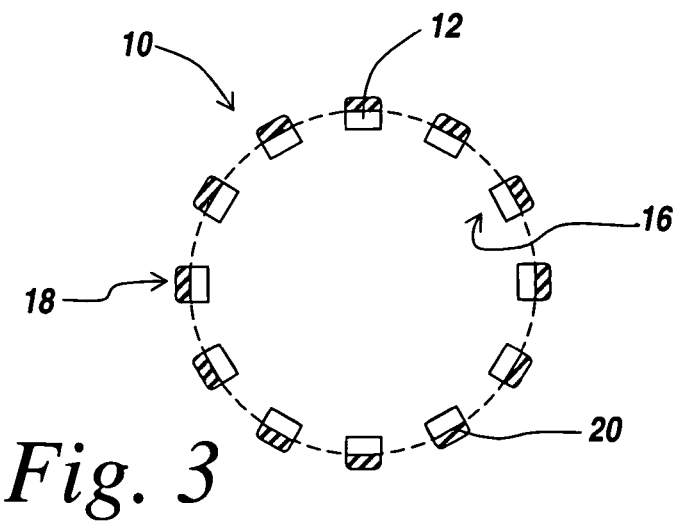
FIG. 3 is a cross-sectional view of the medical device in accordance with another aspect of the present invention.

FIG. 2 illustrates one example embodiment of the stent 10 having a coating 20 applied thereon in accordance with an aspect of the present invention. FIG. 3 is likewise an alternative embodiment of the stent 10 having the coating 20 also applied thereon. The coating 20 is applied to the medical device, such as the stent 10, to provide the stent 10 with different surface properties, and also to provide a vehicle for therapeutic applications.

In FIG. 2, the coating 20 is applied on both the interior surface 16 and the exterior surface 18 of the strut 12 forming the stent 10. In other words, the coating 20 in FIG. 2 substantially encapsulates the struts 12 of the stent 10. In FIG. 3, the coating 20 is applied only on the exterior surface 18 of the stent 10, and not on the interior surface 16 of the stent 10. The coating 20 in both configurations is the same coating; the difference is merely the portion of the stent 10 that is covered by the coating 20. One of ordinary skill in the art will appreciate that the coating 20 as described throughout the Description can be applied in both manners shown in FIG. 2 and FIG. 3, in addition to other configurations such as, partially covering select portions of the stent 10 structure. All such configurations are described by the coating 20 reference.

In some instances of the resulting coated medical device, the stent 10 includes the coating 20, which is bio-absorbable. The coating 20 has a bio-absorbable carrier component, and can also include a therapeutic agent component that can also be bio-absorbable. When applied to a medical device such as a stent 10, it is often desirable for the coating to inhibit or prevent restenosis. Restenosis is a condition whereby the blood vessel experiences undesirable cellular remodeling after injury. When a stent is implanted in a blood vessel, and expanded, the stent itself may cause some injury to the blood vessel. The treated vessel typically has a lesion present which can contribute to the inflammation and extent of cellular remodeling. The end result is that the tissue has an inflammatory response to the conditions. Thus, when a stent is implanted, there is often a need for the stent to include a coating that inhibits inflammation, or is non-inflammatory, and prevents restenosis. These coatings have been provided using a number of different approaches as previously described in the Background. However, none of the prior coatings have utilized a bio-absorbable carrier component to create a bio-absorbable coating with suitable non-inflammatory properties for controlled release of a therapeutic agent.

In some instances of the resultant coated medical device, the bio-absorbable carrier component is in the form of a naturally occurring oil. An example of a naturally occurring oil is fish oil or cod liver oil. A characteristic of the naturally occurring oil is that the oil includes lipids, which contributes to the lipophilic action that is helpful in the delivery of therapeutic agents to the cells of the body tissue. In addition, the naturally occurring oil includes omega-3 fatty acids in accordance with several embodiments of the present invention. As previously described, omega-3 fatty acids and omega-6 fatty acids are known as essential fatty acids. Omega-3 fatty acids can be further characterized as eicosapentaenoic acid (EPA), docosahexanoic acid (DHA), and alpha-linolenic acid (ALA). Both EPA and DHA are known to have anti-inflammatory effects and wound healing effects within the human body.

In further detail, the term "bio-absorbable" generally refers to having the property or characteristic of being able to penetrate the tissue cells of a patient's body. The bio-absorbable coating contains lipids, many of which originate as triglycerides. It has previously been demonstrated that triglyceride products such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Vitamin E compound can also integrate into cellular membranes resulting in decreased membrane fluidity and cellular uptake.

It is also known that damaged vessels undergo oxidative stress. A coating containing an antioxidant such as alpha-tocopherol may aid in preventing further damage by this mechanism.

It should be noted that as utilized herein to describe the present invention, the term vitamin E and the term alpha-tocopherol, are intended to refer to the same or substantially similar substance, such that they are interchangeable and the use of one includes an implicit reference to both. Further included in association with the term vitamin E are such variations including but not limited to one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof. It should also be noted that other antioxidants may be used as a substitute to fulfill the functions of Vitamin E in this coating.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol are accommodated by the coating of the present invention described herein. Accordingly, fatty acids and alpha-tocopherol can be combined in differing amounts and ratios to contribute to a coating in a manner that provides control over the cellular uptake characteristics of the coating and any therapeutic agents mixed therein.

It should further be emphasized that the bio-absorbable nature of the carrier component and the resulting coating (in the instances where a bio-absorbable therapeutic agent component is utilized) results in the coating 20 being removed from the device and substantially absorbed over time by the cells of the body tissue. In short, the coating 20 is generally composed of fatty acids, including in some instances omega-3 fatty acids, bound to glycerol to form mono, di and triglycerides, potentially also including a mixture of free fatty acids and vitamin E. The triglycerides are broken down by lipases (enzymes) which result in free fatty acids that can then be transported across cell membranes. Subsequently, fatty acid metabolism by the cell occurs to metabolize any substances originating with the coating. The bio-absorbable nature of the coating thus results in the coating being absorbed, leaving only an underlying delivery or other medical device structure. There is no substantial foreign body response to the bio-absorbable carrier component, including no substantial inflammatory response. The oils may be modified from a more liquid physical state to a more solid, but still flexible, physical state through the curing process. As the oils are cured, especially in the case of fatty acid-based oils such as fish oil, cross-links form creating a gel. As the curing process is performed over increasing time durations and/or increasing temperature conditions, more cross-links form transitioning the gel from a relatively liquid gel to a relatively solid-like, but still flexible, gel structure.

The coating can also include a therapeutic agent component. The therapeutic agent component mixes with the bio-absorbable carrier component as described later herein. The therapeutic agent component can take a number of different forms including but not limited to anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, therapeutic agents, tissue absorption enhancers, anti-adhesion agents, germicides, antiseptics, proteoglycans, GAG's, gene delivery (polynucleotides), polysaccharides (e.g., heparin), anti-migratory agents, pro-healing agents, ECM/protein production inhibitors, analgesics, prodrugs, and any additional desired therapeutic agents such as those listed in Table 1 below.

TABLE #1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates, cyclosporine, vocolosporine |
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine, vocolosporine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibitation of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae |

TABLE #1-continued

| CLASS | EXAMPLES |
| --- | --- |
| | byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma-1b, Interluekin-10 |
| Immunosuppressive/Immunomodulatory Agents | Cyclosporine, rapamycin, mycophenolate motefil, leflunomide, tacrolimus, tranilast, interferon gamma-1b, mizoribine, vocolosporine |
| Chemotherapeutic Agents | Doxorubicin, paclitaxel, tacrolimus, sirolimus, fludarabine, ranpirnase |
| Tissue Absorption Enhancers | Fish oil, squid oil, omega-3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative, a rapamycin derivative, everolimus, seco-rapamycin, seco-everolimus, and simvastatin, as well as derivatives and prodrugs of any of these examples and any of the above noted agents. Depending on the type of therapeutic agent component added to the coating, the resulting coating can be bio-absorbable if the therapeutic agent component is also bio-absorbable. As described in the Summary of the Invention, the present invention relates to coating a medical device. The coating can be formed of at least two primary components, namely a bio-absorbable carrier component and a therapeutic agent component. The therapeutic agent component has some form of therapeutic or biological effect. The bio-absorbable carrier component can also have a therapeutic or biological effect. It should again be noted that the bio-absorbable carrier component is different from the conventional bio-degradable substances utilized for similar purposes. The bio-absorbable characteristic of the carrier component enables the cells of body tissue of a patient to absorb the bio-absorbable carrier component itself, rather than breaking down the carrier component into inflammatory by-products and disbursing said by-products of the component for ultimate elimination by the patient's body. Accordingly, drug dosages to the patient do not need to be increased to additionally compensate for inflammation caused by the carrier component, as is otherwise required when using polymer-based carriers that themselves cause inflammation.

It should also be noted that the present description makes use of the stent 10 as an example of a medical device that can be coated with the coating 20 of the present invention. However, the present invention is not limited to use with the stent 10. Instead, any number of other implantable medical devices can be coated in accordance with the teachings of the present invention with the described coating 20. Such medical devices include catheters, grafts, balloons, prostheses, stents, other medical device implants, and the like. Implantation refers to both temporarily implantable medical devices, as well as permanently implantable medical devices. In the instance of the example stent 10, a common requirement of stents is that they include some substance or agent that inhibits restenosis. Accordingly, the example coating 20 as described is directed toward the reduction or the elimination of restenosis. However, one of ordinary skill in the art will appreciate that the coating 20 can have other therapeutic or biological benefits. For example, the coating 20 can alternately be used as a lubricant that eases the insertion of a device or minimizes irritation caused by a device. The composition of the coating 20 is simply modified or mixed in a different manner to result in a different biological or physical effect.

Figure 4:
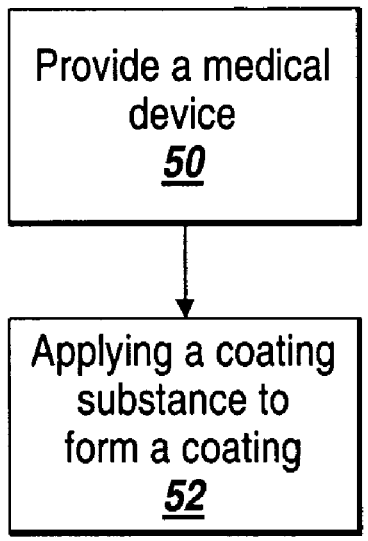
FIG. 4 is a flow chart illustrating a method of making a coated medical device, in accordance with one embodiment of the present invention.

FIG. 4 illustrates one method of making a coated medical device, in the form of the coated stent 10. The process involves providing a medical device, such as the stent 10 (step 50). A coating, such as coating 20, is then applied to the medical device (step 52). One of ordinary skill in the art will appreciate that this basic method of application of a coating to a medical device such as the stent 10 can have a number of different variations falling within the process described. Depending on the particular application, the stent 10 with the coating 20 applied thereon can be implanted after the coating 20 is applied, or additional steps such as curing, sterilization, and removal of solvent can be applied to further prepare the stent 10 and coating 20. Furthermore, if the coating 20 includes a therapeutic agent that requires some form of activation (such as UV light), such actions can be implemented accordingly.

In one embodiment of the present invention, applying the coating to the medical device involves using an applicator to apply the coating. The use of an applicator allows for application of a coating having improved uniformity and coverage. An exemplary method of this can be seen in FIG. 5. The method involves providing a medical device onto which a coating is to be applied (step 202); providing a coating substance for application onto the medical device (step 204); and applying the coating substance to the medical device using an applicator (step 206). In certain embodiments, the method may further include the step of curing the coating substance to form a coating on the medical device (step 208).

Figure 6A:
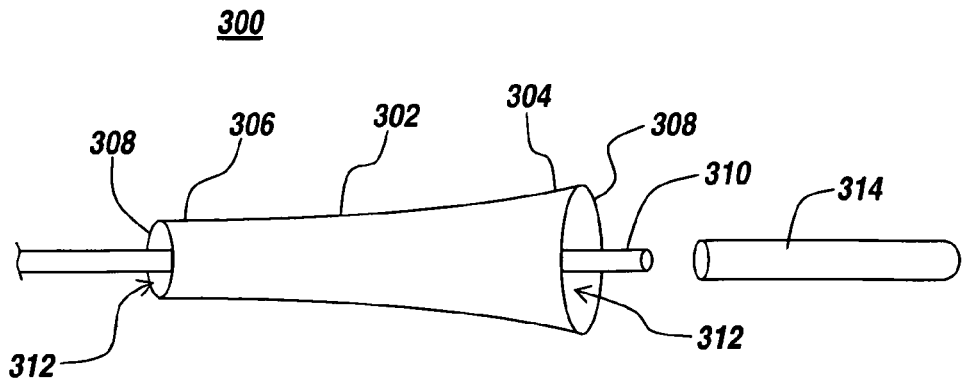
FIG. 6A is a diagrammatic illustration of an applicator in accordance with one embodiment of the present invention.
Figure 6B:
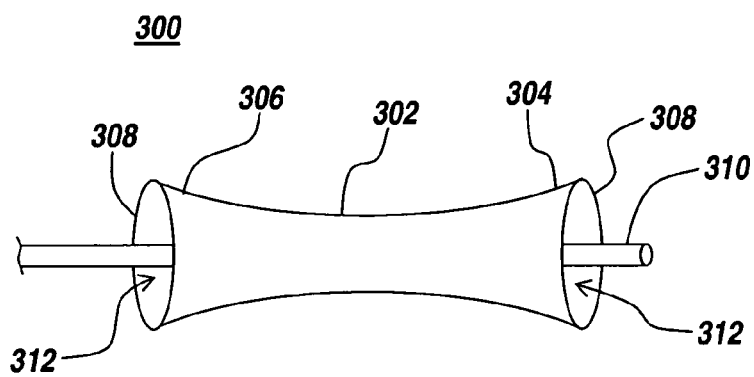
FIG. 6B is a diagrammatic illustration of an applicator in accordance with another embodiment of the present invention.
Figure 6C:
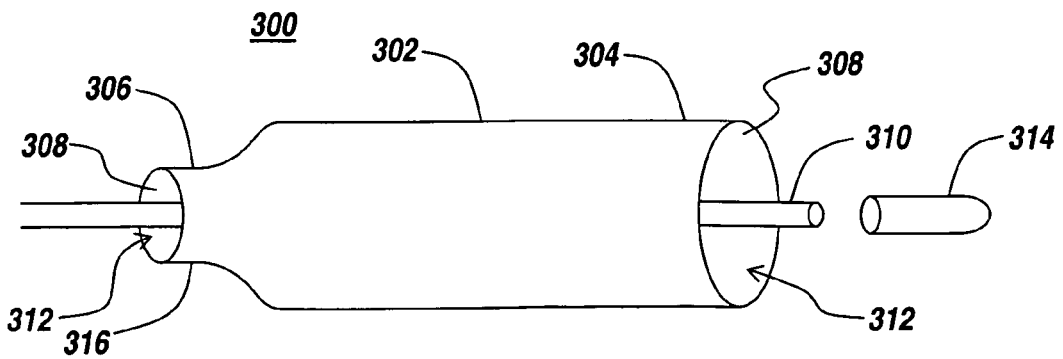
FIG. 6C is a diagrammatic illustration of an applicator in accordance with another embodiment of the present invention.

An exemplary embodiment of an applicator 300 can be seen in FIG. 6A. The applicator 300 is formed of a sheath 302 having a first end 304, a second end 306 and a lumen 308 between the first 304 and second 306 ends. The first end 304 is flared and has a cross-sectional area greater than a cross sectional area of a portion of the lumen 308. The sheath 302 is sized and dimensioned to fit over the medical device 310, while providing a clearance 312 between the sheath 302 and the medical device 310 for receiving a coating substance for application to the medical device 310. In some embodiments, the second end 306 may also be flared and have a cross-sectional area greater than a cross-sectional area of at least a portion of the lumen 308, as can be seen in FIG. 6B. In some embodiments, the second end 306 may also be necked down and have a cross-sectional area less than a cross-sectional area of at least a portion of the lumen 308, as can be seen in FIG. 6C. The length of the land 316 on the necked down section of the second end 306 of the applicator 300 can be sized to deposit a consistent coating weight. The first end 304 can optionally be flared to ease the passage over the device 310. Examples of medical devices 310 on which the applicator 300 may be used include stents and catheters. In certain embodiments, a coating is applied to a stent that has been positioned on the end of a catheter. Preferably, the applicator 300 is formed of plastic but other suitable material that can be formed into the desired configuration can be used. This particular coating method can be used for any device which is substantially cylindrical in geometry, such as devices like guide wires, stylets, stents, as well as grafts, fibers, and the like.

In the present embodiment the cross-sectional shape of the applicator is circular giving the applicator a funnel or trumpet like shape. Other suitable cross sectional shapes include polygonal shapes such as hexagonal, octagonal, or the like, expandable cross sections that contact the device or change dimensions as they pass over the device, and/or irregular shapes such as fingers or bristles that wipe off excess coating. Other possible shapes and configurations will be apparent to one skilled in the art given the benefit of this disclosure.

In use, the coating is applied by placing the applicator 300 onto the medical device 310 and then filling the applicator 300 with the coating substance. The flared nature of the first end 304 assists in providing a larger opening for receiving the coating substance and directing it onto the medical device. The coating substance may be placed into the applicator 300, for example, at flared first end 304, or be placed onto the medical device 310 directly. In certain embodiments the coating substance is delivered using a metering device, such as a dispenser, so that the amount of coating, and in certain cases, dosage of a therapeutic agent, can be controlled. In other embodiments, the design, dimensions and material properties of the applicator can be used to control the dosage of a therapeutic agent.

In the present embodiment the applicator 300 is configured to slide onto or over the medical device 310. In other embodiments, the applicator 300 may be formed of two halves that are joined together around the medical device 310. Other possible configurations will be apparent to one skilled in the art given the benefit of this disclosure.

In certain embodiments, after the applicator 300 has been filled with coating substance, the applicator 300 can be removed. In the present embodiment, wherein the applicator 300 is configured to slide onto the medical device 310, removing the applicator 300 is performed by sliding the applicator 300 off the medical device 310. Alternately, the coating substance may be applied directly to the medical device 310 and the applicator 300 is then slid over the medical device 310 to spread the coating substance over the medical device 310. In this embodiment, the clearance between the sheath 302 or the applicator land 316 and the medical device 310 is dimensioned and sized to leave a residual coating of the coating substance on the medical device 310 as the applicator 300 is slid over the medical device 310. Preferably, the clearance is between 0.0001 to 0.1 inches. More preferably, the clearance is between 0.001 to 0.01 inches. In other embodiments, the applicator can make contact with the device surface. In certain embodiments the uniformity and coverage of such a residual coating can be improved by sliding the applicator 300 over the medical device 310 with a twisting motion.

Figure 5:
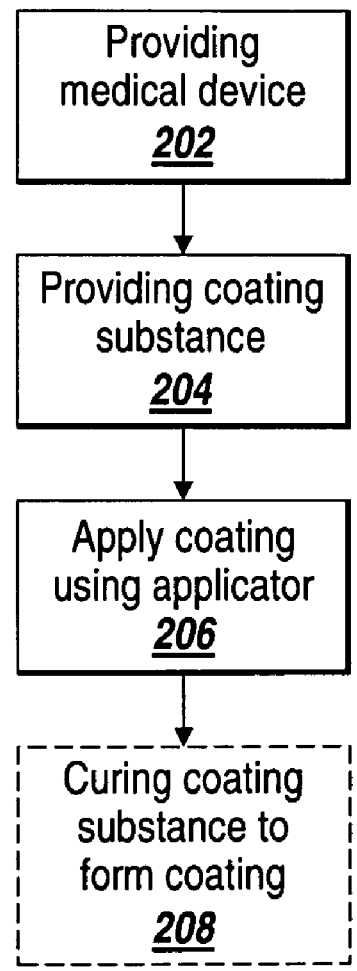
FIG. 5 is a flow chart illustrating a variation of the method of FIG. 4 using an applicator in accordance with one embodiment of the present invention.

In certain embodiments, as set forth in step 208 of FIG. 5, once the coating substance has been applied to the medical device, the coating substance is cured or activated to form the coating on the medical device. Curing can be performed after the applicator has been removed, or with the applicator still in place over the medical device. Curing or activating with respect to the present invention generally refers to thickening, hardening, or drying of a material brought about by heat, UV, reactive gases, exposure to air, or chemical means.

In some embodiments, once the coating has been formed on the medical device 310, a protective sleeve 314 is placed over the medical device 310 to protect the coating on the medical device 310 during further handling. In an exemplary embodiment, the protective sleeve 314 is formed of plastic, and sized and dimensioned to fit over the medical device 310. Other suitable implementations will be apparent to one skilled in the art given the benefit of this disclosure.

In certain embodiments wherein a coating is being applied to a catheter, a cap, such as a coating cap or cap stylet, may be used when applying the coating substance. When placed on the end of a catheter, the cap prevents coating substance from penetrating the lumen at the end of the catheter. A cap stylet can be a section of tubing diametrically designed to fit over the end of the catheter and long enough to prevent coating material from flowing into the catheter lumen. An exemplary embodiment of such a method can be seen in FIG. 7. In this embodiment, the method involves providing a catheter onto which a coating is to be applied (step 402), providing a coating substance for application onto the catheter (step 404), providing a cap configured to fit onto an end of the catheter (step 406); placing the cap onto an end of the catheter (step 408), and applying the coating substance onto the catheter (step 410).

The cap comprises a section of tubing configured to fit on the end of the catheter to seal the lumen at the end of the catheter during the application of a coating. The cap can optionally be attached to a stylet, as in the case with a cap stylet or the cap can be separate from the stylet. The cap can optionally be closed on one end. An exemplary embodiment of a cap and its interaction with a catheter can be seen in FIG. 8. In this embodiment the cap is a cap stylet 500. The catheter 520 has a proximal end (not shown), a distal end 522, and a lumen 524 between the proximal and distal ends. The cap stylet 500 features a stylet 502 configured to fill the lumen 524 of the catheter 520; and a section of tubing 504 attached to the stylet 502 sized and dimensioned to be fitted on the end of the catheter 520 to seal the lumen 524 of the catheter 520. In certain embodiments, the section of tubing 504 is sized to pinch fit on the end of a catheter 520. Alternately, the cap can snap or interference fit on the end of the catheter. When placed on the end of a catheter 520, the cap stylet 500 prevents the coating substance from wicking into the lumen 524 at the end of the catheter 520 as a coating is applied. If the coating substance gets into the lumen 524 it could create an obstruction that may adversely effect the operation of the catheter 520. Preferably, the cap stylet 500 is placed on the distal end 522 of the catheter 520, which is to be inserted into a patient, and is thus coated. In certain embodiments wherein the whole catheter is to be coated, a cap stylet 500 can be placed on each end of the catheter 520.

Figure 7:
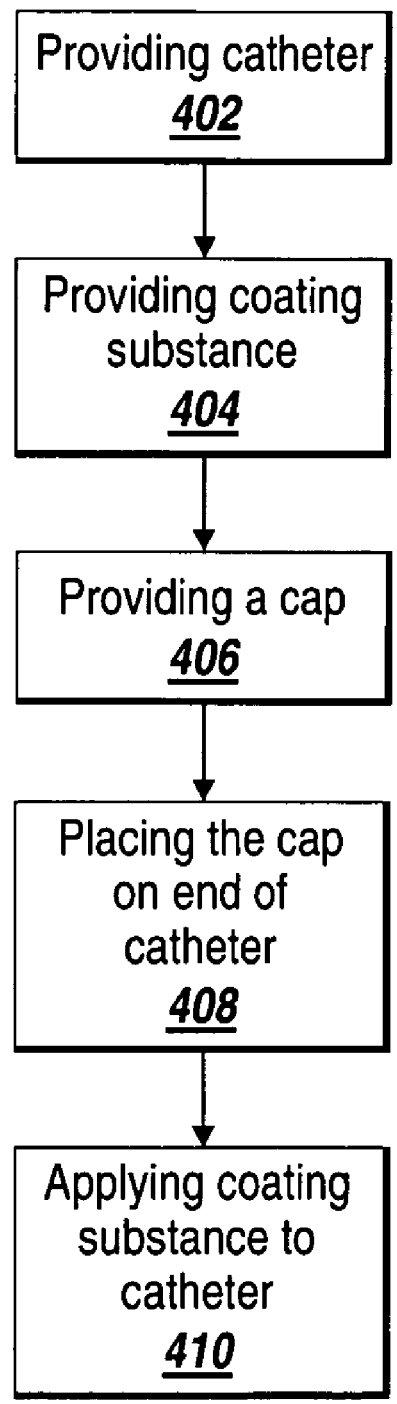
FIG. 7 is a flow chart illustrating a variation of the method of FIG. 4 using a cap stylet in accordance with one embodiment of the present invention.
Figure 8:
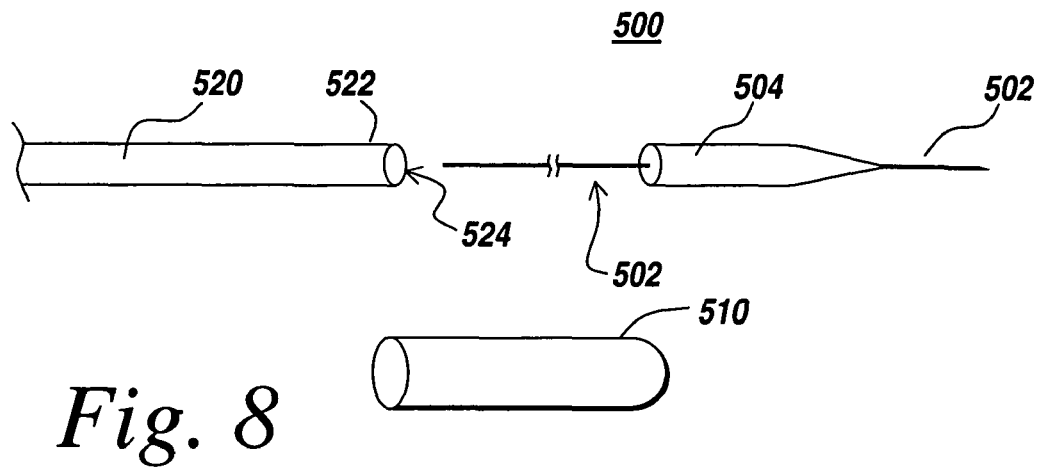
FIG. 8 is a diagrammatic illustration of a cap stylet in accordance with one embodiment of the present invention.

Once the cap, in this case a cap stylet 500, has been placed on the end of the catheter 520, the coating can then be applied to the catheter (step 410 of FIG. 7). In certain embodiments this involves using an applicator as set forth above. The coating may also be applied by dip coating (including submersing, surrounding, bathing), spray coating, printing, wiping, electrostatic coating, brushing, painting, pipetting, or any means suitable for applying the coating substance.

Once the coating substance has been applied, the coating substance can then be cured as discussed above. Likewise, in some embodiments a protective sleeve 510 may be placed on the catheter 520 to protect the coating.

Figure 9:
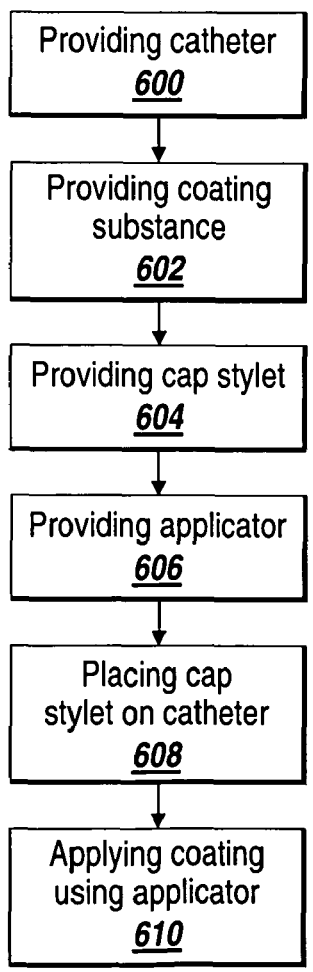
FIG. 9 is a flow chart illustrating a method of applying a coating to a catheter using an applicator and cap stylet in accordance with one embodiment of the present invention.

Another exemplary embodiment of a method, wherein an applicator and a cap stylet are used in forming a coating on a catheter, can bee seen in FIG. 9. In this embodiment, the method includes providing a catheter (step 600), providing the coating substance for application onto the catheter (step 602), providing a cap stylet configured to fit onto an end of the catheter (step 604), providing an applicator configured to apply a coating to the catheter (step 606), placing the cap stylet onto an end of the catheter (step 608) and applying the coating substance onto the catheter using the applicator (step 610).

Figure 10:
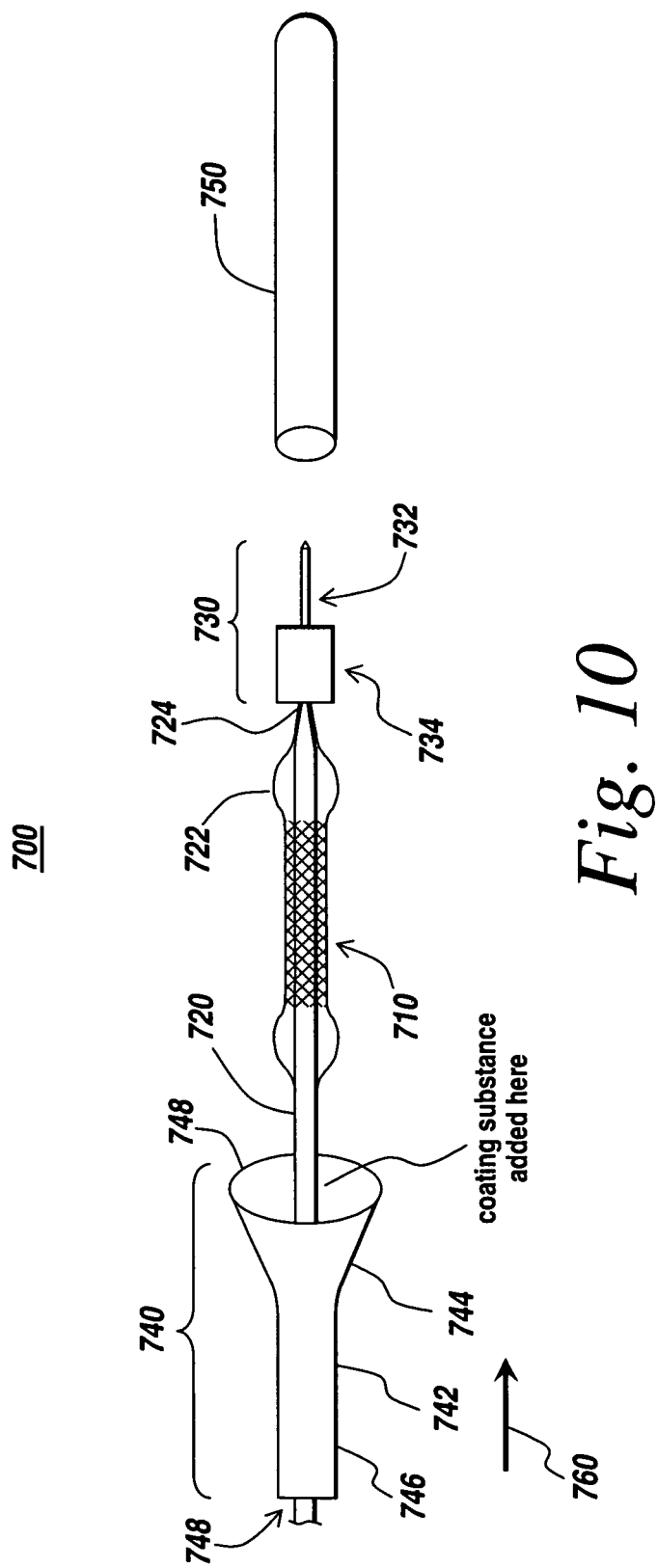
FIG. 10 is a diagrammatic illustration of the interaction of a catheter, applicator, and cap stylet in accordance with one embodiment of the present invention.

The methodology of FIG. 9 may be better understood if viewed in conjunction with the exemplary embodiment of FIG. 10 of a system 700 for applying a coating to a medical device. In this instance, a catheter 720 has a stent 710 pre-positioned on the distal end 722 of the catheter for implantation in a patient. A cap stylet 730 is placed onto the distal end 722 of the catheter 720. The cap stylet 730 features a stylet 732 configured to fill a lumen 724 of the catheter 720, and a section of tubing 734 optionally attached to the stylet 732 sized and dimensioned to be fitted on an end of the catheter 720 to seal the lumen 724 of the catheter 720. An applicator 740 is then slid onto the catheter 720 beyond the stent 710. The applicator 740 features a sheath 742 having a first end 744, a second end 746 and a lumen 748 between the first 744 and second 746 ends. The first end 744 is optionally flared and has a cross-sectional area greater than a cross-sectional area of at least a portion of the lumen 748. The second end 746 is optionally necked down to a dimension less than the cross sectional area of at least a portion of the lumen 748. The sheath 742 is sized and dimensioned to fit over the catheter 720, providing a clearance between the sheath 742 and the catheter 720 for receiving a coating substance for application to the catheter. The coating substance is then applied. In this embodiment, the applicator 740 is filled with coating substance at the flared first end 744 using a metering device, such as a dispenser, to ensure the proper amount of coating substance is applied. Alternately, the coating substance may be applied directly to the catheter 720 or the stent 710. The applicator 740 is then slid off the catheter 720 over the stent 710 while optionally removing the cap stylet 730 in the direction of arrow 760 using, for example, a twisting motion. The clearance between the sheath 742 and the catheter 720 is sized and dimensioned to leave a residual coating of the coating substance as the applicator 740 is slid over the catheter 720. In another embodiment, the clearance between the optionally necked down second end 746 of the sheath 742 and the catheter 720 is sized and dimensioned to leave a residual coating of the coating substance as the applicator 740 is slid over the catheter 720.

In certain embodiments, once the coating substance has been applied, the coating substance may be cured as discussed above. Likewise, a protective sleeve 750 can be placed over the catheter 720 and stent 710 to protect the coating during further handling.

Figure 11:
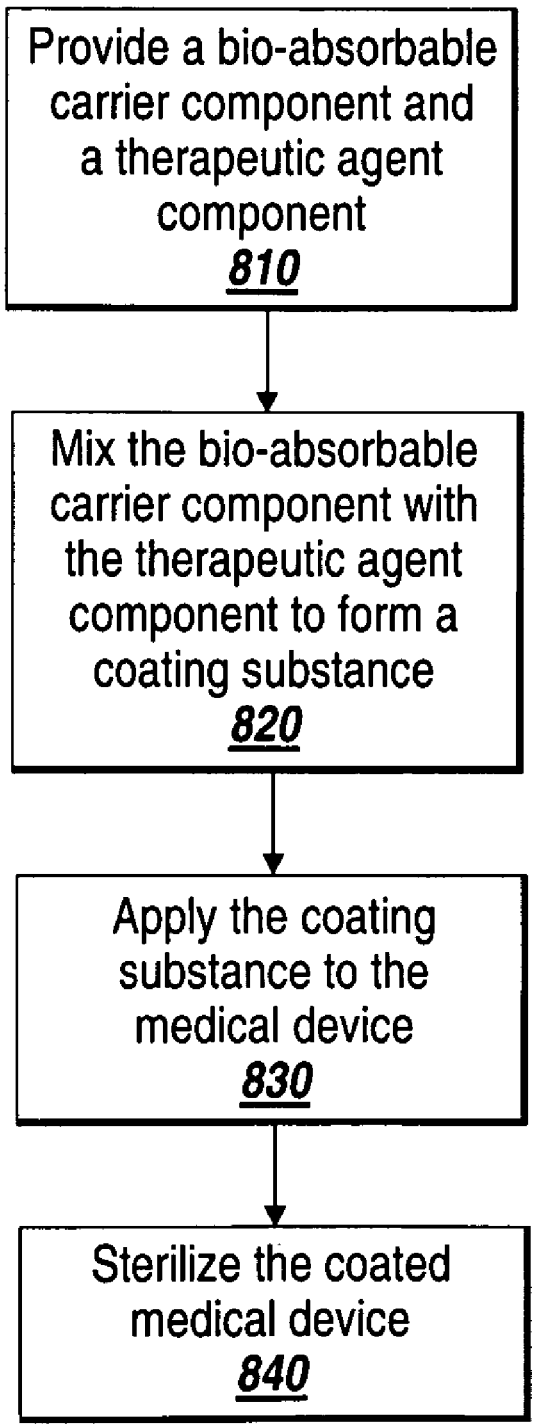
FIG. 11 is a flow chart illustrating a variation of the method of FIG. 4, in accordance with one embodiment of the present invention.

FIG. 11 is a flowchart illustrating another example implementation of the method of FIG. 4. In accordance with the steps illustrated in FIG. 11, a bio-absorbable carrier component is provided along with a therapeutic agent component (step 810). The provision of the bio-absorbable carrier component and the provision of the therapeutic agent component can occur individually, or in combination, and can occur in any order or simultaneously. The bio-absorbable carrier component is mixed with the therapeutic agent component (or vice versa) to form a coating substance (step 820). The coating substance is applied to the medical device, such as a stent or catheter, to form the coating (step 830). The coated medical device is then sterilized using any number of different sterilization processes (step 840). For example, sterilization can be implemented utilizing ethylene oxide, gamma radiation, E beam, steam, gas plasma, or vaporized hydrogen peroxide. One of ordinary skill in the art will appreciate that other sterilization processes can also be applied, and that those listed herein are merely examples of sterilization processes that result in a sterilization of the coated stent, preferably without having a detrimental effect on the coating 20. Furthermore, one of ordinary skill in the art will appreciate that the coating and device can be sterilized separately and then the coating applied in a sterile field.

Figure 12:
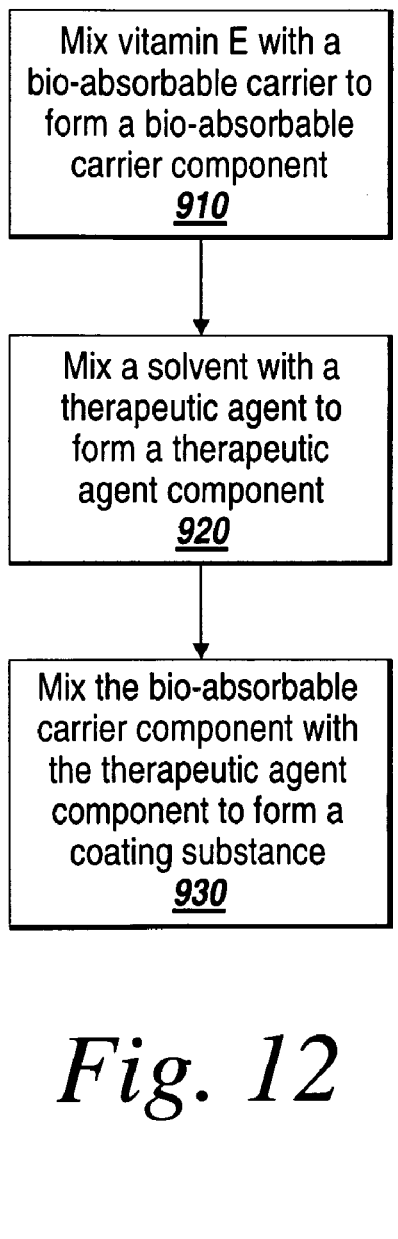
FIG. 12 is a flow chart illustrating another variation of the method of FIG. 4, in accordance with one embodiment of the present invention.
Figure 13:
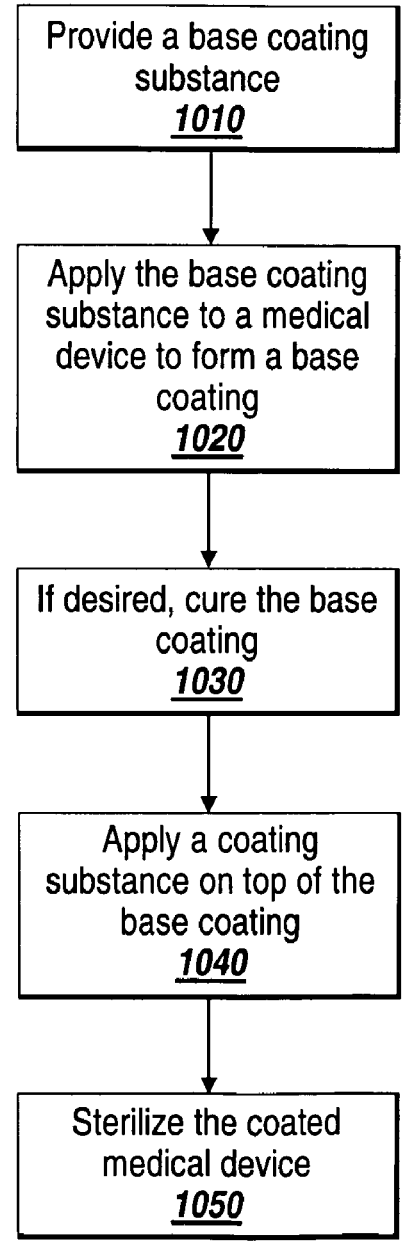
FIG. 13 is a flow chart illustrating another variation of the method of FIG. 4, in accordance with one embodiment of the present invention.

The formation of the bio-absorbable carrier component and the therapeutic agent component can be done in accordance with different methods. FIG. 12 is a flow chart illustrating one example method for forming each of the components. Vitamin E is mixed with a bio-absorbable carrier to form a bio-absorbable carrier component (step 910). A solvent is mixed with a therapeutic agent to form a therapeutic agent component (step 920). The solvent can be chosen from a number of different alternatives, including, but not limited to, ethanol or N-Methyl-2-Pyrrolidone (NMP). The bio-absorbable carrier component is then mixed with the therapeutic agent component to form the coating substance (step 930). The solvent can then be removed with vacuum or heat. It should be noted that the preparation of the bio-absorbable carrier component and the therapeutic agent component can be done in either order, or substantially simultaneously. Additionally, in an alternative approach, the solvent can be omitted altogether.

Figure 14:
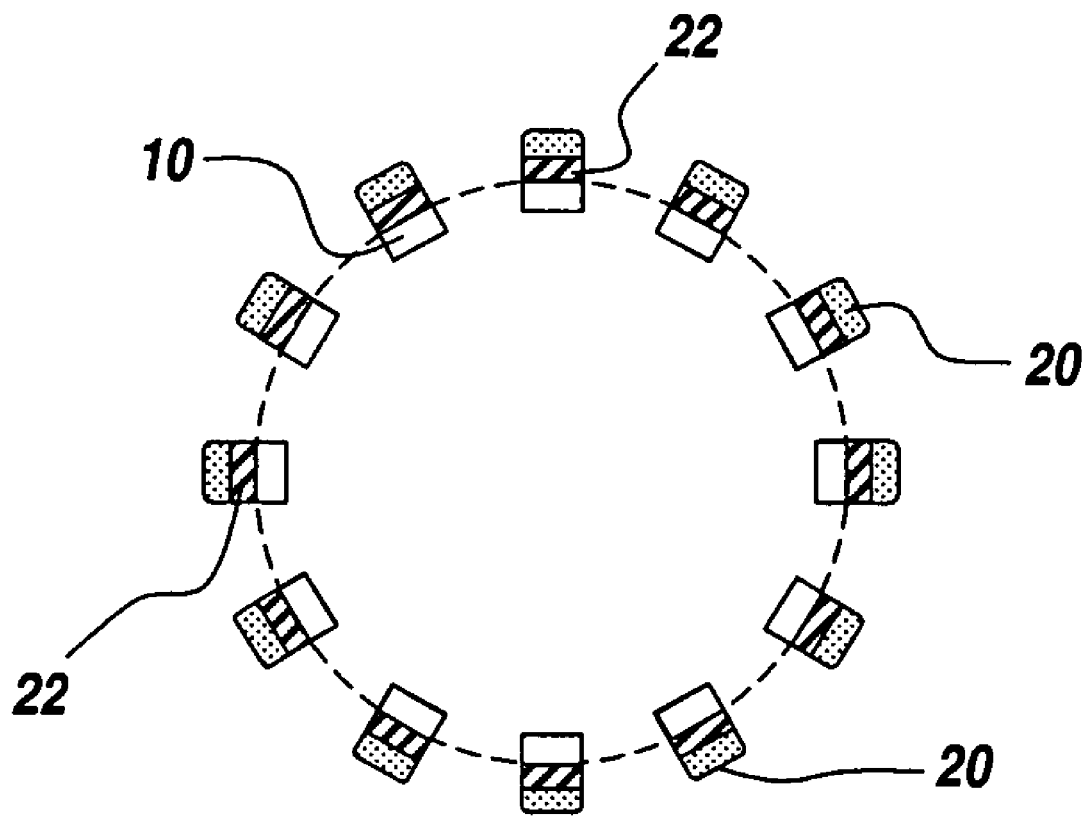
FIG. 14 is a cross sectional view of a coated medical device in accordance with one embodiment of the present invention.

In accordance with another technique, a surface preparation or pre-treatment 22, as shown in FIG. 14, is provided on a stent 10. More specifically and in reference to the flowchart of FIG. 13, a pre-treatment substance or base coating is first provided (step 1010). The surface treatment may include any surface preparation technique designed to improve adhesion and/or uniformity. Examples include gas plasma deposition, surface cleaning, etching, roughening, etc. The pre-treatment substance or base coating is applied to a medical device, such as the stent 10, to prepare the medical device surface for application of the coating (step 1020). If desired, the pre-treatment or base coating 22 is cured (step 1030). Curing methods can include processes such as application of UV light, heat, reactive gases, or chemical means to cure the pre-treatment 22. A coating substance is then applied on top of the pre-treatment 22 (step 1040). The coated medical device is then sterilized using any number of sterilization processes as previously mentioned (step 1050).

FIG. 14 illustrates the stent 10 having two coatings, specifically, the pre-treatment 22 and the coating 20. The pre-treatment 22 serves as a base or primer for the coating 20. The coating 20 conforms and adheres better to the pre-treatment 22 than it conforms and adheres directly to the stent 10, especially if the coating 20 is not heat or UV cured. The pre-treatment can be formed of a number of different materials or substances. In accordance with one example embodiment of the present invention, the pre-treatment is formed of a bio-absorbable substance, such as a naturally occurring oil (e.g., fish oil). The bio-absorbable nature of the pre-treatment 22 results in the pre-treatment 22 ultimately being absorbed by the cells of the body tissue after the coating 20 has been absorbed.

Figure 15:
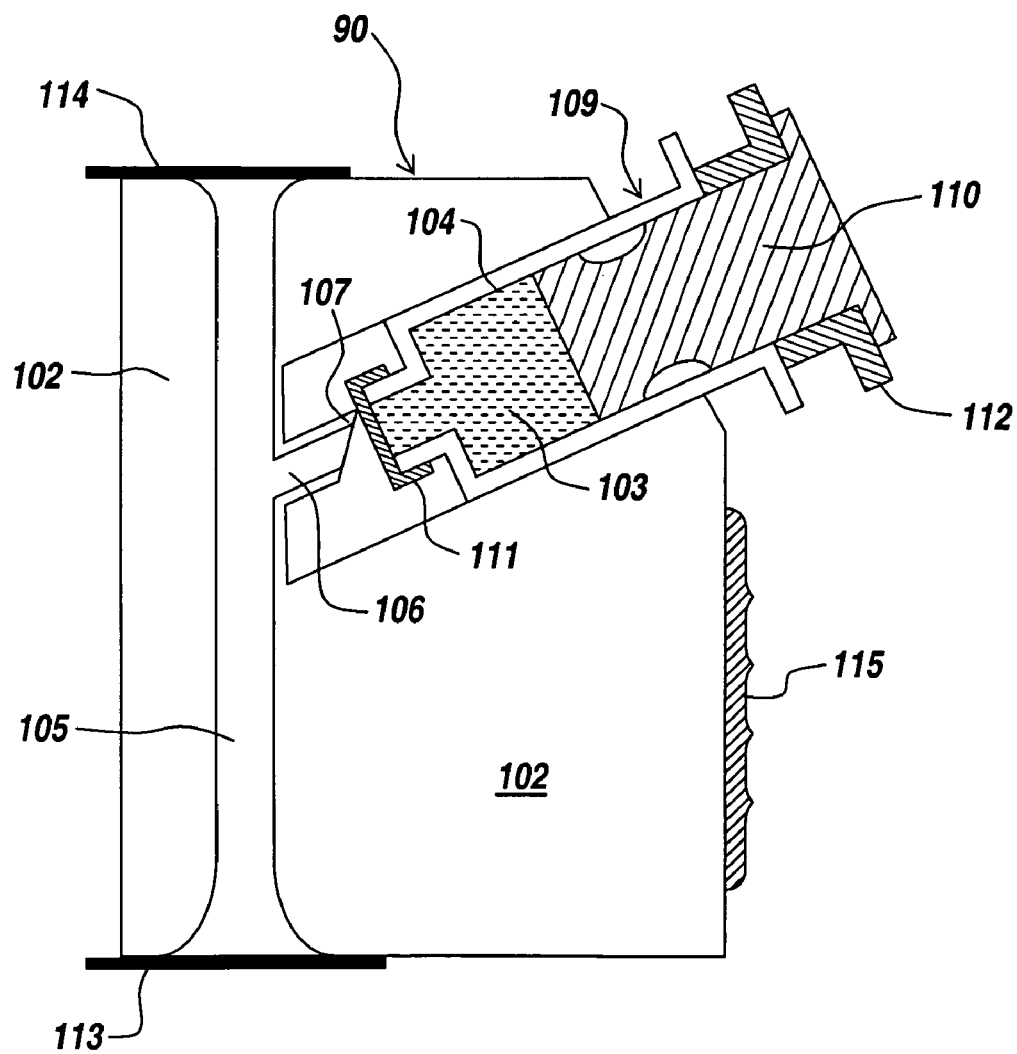
FIG. 15 is a diagrammatic illustration of an apparatus for coating a medical device including a dispenser, in accordance with one embodiment of the present invention.

FIG. 15 diagrammatically illustrates a coating apparatus 90 in accordance with an embodiment of the present invention. The various elements of the apparatus 90 are disposed in the housing 102. The housing 102 can be formed of a polymer based material, a glass, a metal, a combination of the aforementioned or any other material that can provide sufficient structural integrity and is non-reactive with the coating material. The apparatus 90 may be either single use (disposable) or may be reusable. If the apparatus 90 is to be used more than once, the housing 102 should be formed of a material that can be sterilized.

A sealed reservoir chamber 104 is disposed in the housing 102. As shown in FIG. 15, the reservoir chamber 104 may be contained within a dispenser 109. The walls of the reservoir chamber 104 and a septum 111 at the distal end of the dispenser 109 form a preserving reservoir. The preserving reservoir contains and preserves the coating material. The preserving reservoir is sealed at one end by the septum 111 and is sealed at the opposite end by the plunger 110. A coating material 103 is disposed within the reservoir chamber 104. One of ordinary skill in the art will appreciate that in instances where the coating material 103 does not degrade substantially over time, the preserving reservoir acts more as a storage container, since preservation is not an issue.

The coating material 103 may be composed of any number of the bioabsorbable oils discussed previously. The coating material 103 may also include any number of the therapeutic agents discussed above and appearing in Table #1, as well as their analogs, derivatives, or prodrugs. Other possible coating materials including other oils and other therapeutic agents not explicitly mentioned in this disclosure will be apparent to one skilled in the art given the benefit of this disclosure. Likewise, the coating material 103 may have lubricious characteristics, or provide other desired aspects to the medical device.

An applicator or reducing template 105 is disposed in the housing 102. The reducing template 105 may be formed directly in the housing 102, as is shown in this figure, or may be formed in a separate piece then positioned in the housing 102. The reducing template (e.g., reducing template 105) as described herein may incorporate any of the characteristics of the sheath 302 and lumen 308 of FIGS. 6A, 6B, and 6C and any of the characteristics of the sheath 742 and lumen 748 of FIG. 10, as well as any of the characteristics of the applicators (e.g., applicator 300) as described herein. Specifically, the reducing template 105 disposed in the housing 102 is sized and dimensioned to fit over a medical device, while providing a clearance between the reducing template 105 and the medical device for receiving a coating material 103 for application to the medical device 310. In some instances, the reducing template may have some flexibility, elasticity, or expansion characteristics enabling the reducing template to stretch or expand to fit over the medical device, contacting the medical device. When such an embodiment is implemented, a nominal clearance remains for the coating material between the medical device and the reducing template for the coating material to form the desired coating thickness.

Similar to the applicator or reducing template of other embodiments herein, examples of medical devices on which the apparatus 90 may be used include stents, balloons and catheters. In certain embodiments, a coating is applied to a stent that has been positioned on the end of a catheter. In the embodiment depicted in FIG. 15, the applicator or reducing template 105 has a circular cross-section that increases at both ends giving the reducing template a funnel or trumpet-like shape. In other embodiments, the applicator or reducing template 105 has a circular cross-section that decreases at one or both ends giving the reducing template a necked down or reversed funnel shape. Other suitable cross-sectional shapes include polygonal shapes such as hexagonal, octagonal, or the like. Other possible shapes and configurations will be apparent to one skilled in the art given the benefit of this disclosure.

In the present embodiment, the apparatus 90 is configured to slide onto the medical device. The clearance between the reducing template 105 and the medical device 310 is dimensioned and sized to leave a residual coating of the coating material 103 on the medical device as the apparatus 90 is slid over the medical device. Preferably, the clearance is between 0.0001 to 0.1 inches. More preferably, the clearance is between 0.001 to 0.01 inches. In certain embodiments, the applicator or reducing template can contact the device. In certain embodiments, the uniformity and coverage of such a residual coating can be improved by sliding the apparatus 90 over the medical device with a twisting motion. Alternatively, this may be accomplished by twisting or rotating the medical device while it is inside the applicator or reducing template instead of twisting or rotating the applicator around the medical device.

A reservoir access port 106 fluidly couples the reducing template 105 with the reservoir chamber 104 upon activation of the apparatus 90. In the example embodiment, a retaining ring 112 is removed, a dispenser 109 is pressed into the housing 102 and the plunger 110 of the dispenser 109 is depressed to activate the apparatus. When the dispenser 109 is pushed into the housing 102, a sharp point 107 of the reservoir access port 106, which is a seal breaching mechanism, pierces the septum 111 allowing fluid coupling between the reducing template 105 and the reservoir chamber 104 via the reservoir access port 106. The plunger 110 of the dispenser 109 is further depressed providing a compressive force to move the coating material 103 from the reservoir chamber 104 through the reservoir access port 106 to the reducing template 105. The medical device may already be positioned in the reducing template 105 when the apparatus 90 is activated. Alternatively, the medical device may be inserted into the apparatus 90 after the apparatus 90 is activated.

According to aspects of the present invention, the apparatus 90 may also include a first seal 113 and a second seal 114, which maintain the integrity of an interior of the reducing template 105. The apparatus may also include a grip 115 to facilitate easier handling of the apparatus.

Figure 16:
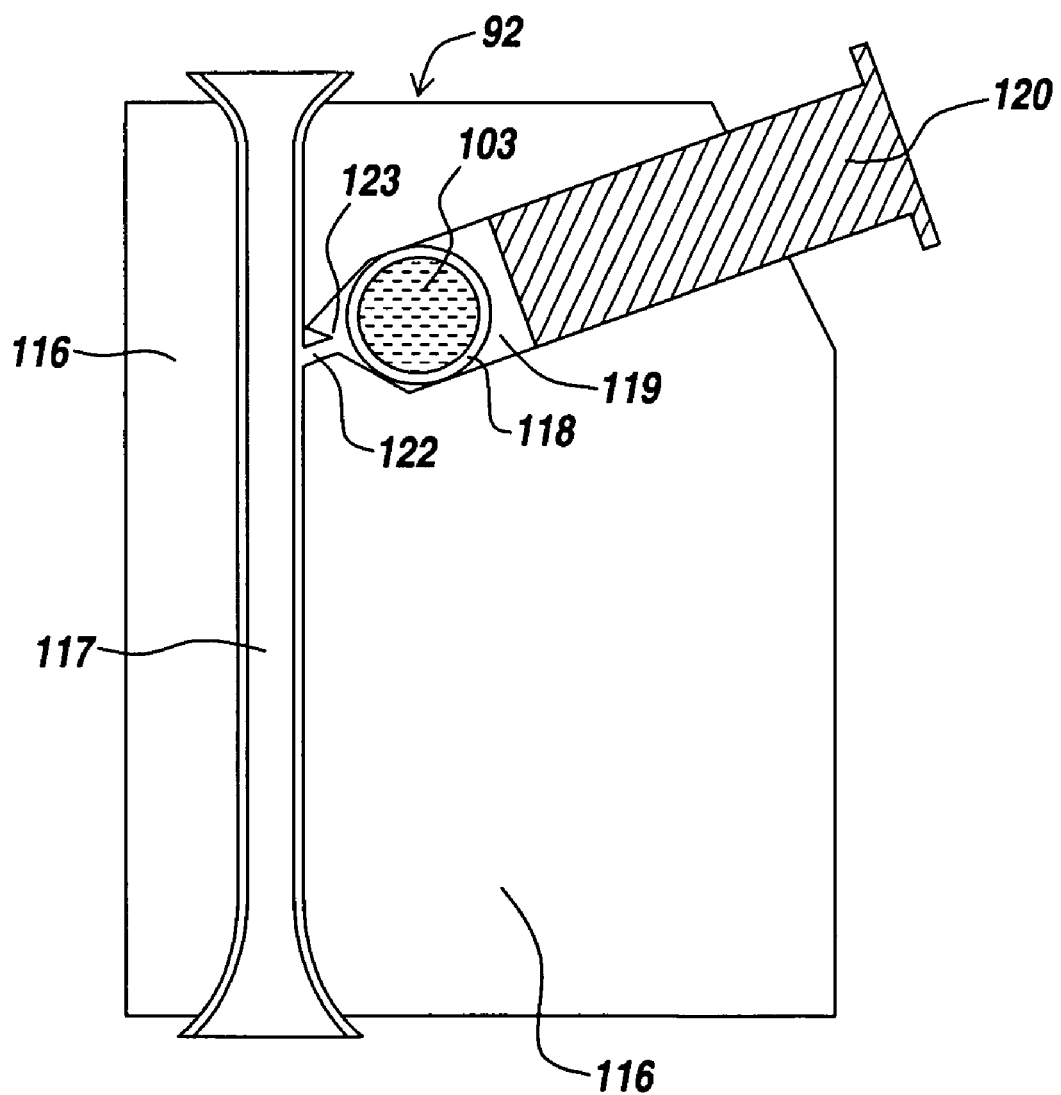
FIG. 16 is a diagrammatic illustration of another apparatus for coating a medical device which includes a pod, in accordance with another embodiment of the present invention.

FIG. 16 diagrammatically illustrates a coating apparatus 92 that includes a sealed pod 118 in accordance with another embodiment of the present invention. The apparatus 92 also includes a housing 116. In this embodiment the reducing template 117 is not formed in one piece with the housing. A sealed reservoir chamber 119 is formed in the housing 116. The reservoir chamber 119 contains a preserving reservoir in the form of the sealed pod 118. The sealed pod 118, which contains the coating material 103, is formed of a material that contains and optionally preserves the coating material 103 within the pod 118. The pod 118 is formed of a material structured such that it can be pierced by the sharp point 123 of the reservoir access port 122, (a seal breaching mechanism) without breaking it into pieces and such that it may be easily deformed by a plunger 120.

A wall of the pod 118 may be formed of any material capable of containing and preserving the coating material without reacting with the coating material. In the preferred embodiment, the pod wall material includes a gelatin. The authors have performed experiments on commercially available Omega-3 complex fish oil capsules to determine the extent of oxidation of oil in the "gel cap" pill when stored at room temperature. A Fourier transform infra-red spectroscopy (FITR) analysis was performed on the oil inside a commercially available Omega-3 complex pill. The FTIR spectroscopy showed no significant oxidation of the highly unsaturated Omega-complex oil that had been stored within the "gel cap" indicating that a gelatin pod can prevent oxidation of omega-3 complex oil. Alternatively, the pod wall material may also include cellulose. One of skill in the art will appreciate that a variety of different materials may be chosen for the pod wall, however, the material chosen for the pod wall must be appropriately matched with the material chosen for the coating material which is to be contained and optionally preserved within the pod when desired, and also must work in conjunction with the remainder of the apparatus 92 to be pierced or otherwise accessed to supply the coating material when desired.

Figure 17:
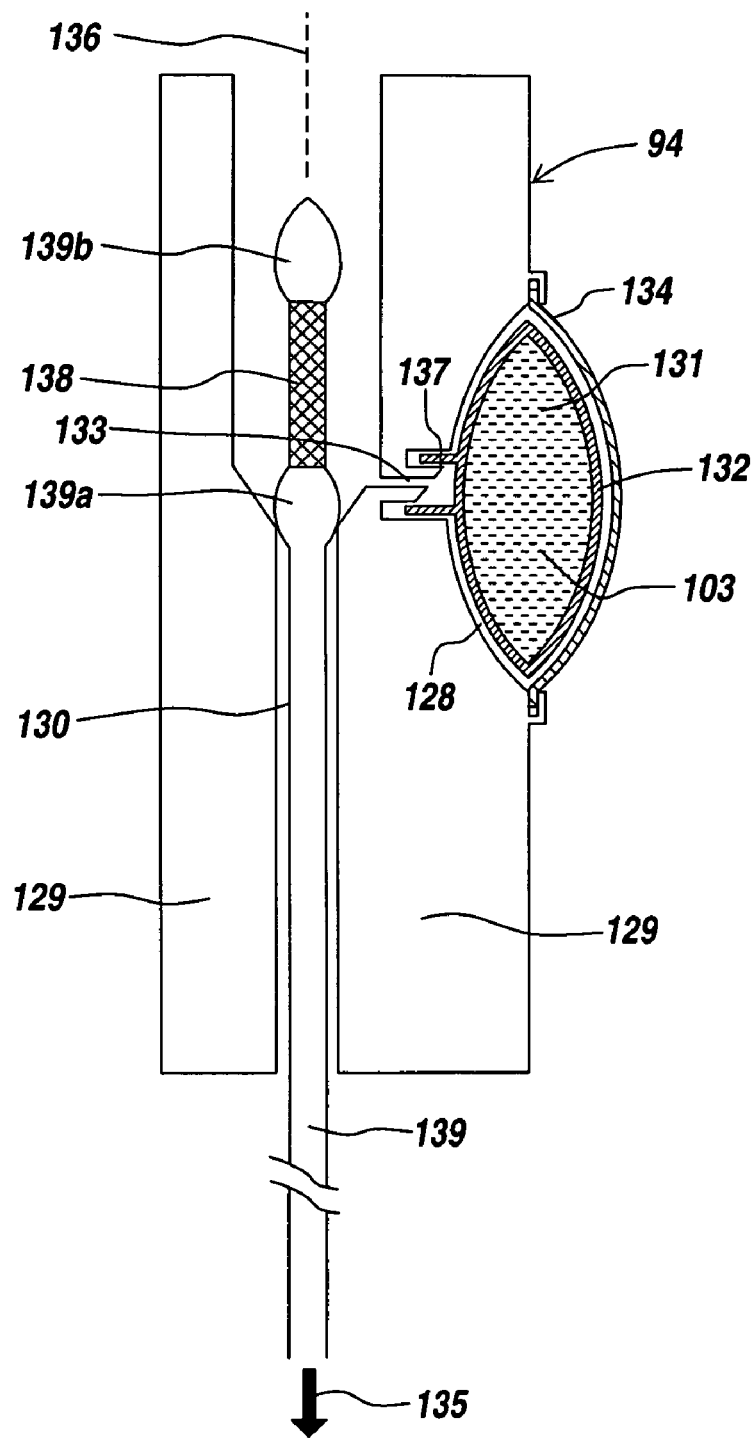
FIG. 17 is a diagrammatic illustration of another apparatus for coating a medical device that employs depression of a flexible member, in accordance with yet another embodiment of the present invention.

FIG. 17 diagrammatically illustrates a coating apparatus 94 that also includes a sealed reservoir chamber 128 and employs depression of a flexible member 134 in accordance with one aspect of another embodiment of the present invention. This embodiment includes a housing 129 with a removable flexible member 134 that forms part of the reservoir chamber 128. The flexible member 134 can be removed allowing access to insert a preserving reservoir in the form of a sealed pod 131 containing coating material 103. Once the sealed pod 131 is inserted, the flexible member 134 is replaced to seal the reservoir chamber 128. A pod wall 132 preserves the coating material 103. The housing 129 includes a reducing template 130 and a reservoir access port 133. A catheter 139 with a mounted medical device 138 (e.g. a mounted stent), is inserted into the reducing template 130 such that a proximal end 139a of the catheter balloon is positioned at the base of the reducing template 130 conic as shown in FIG. 17. The apex of the flexible member 134 is depressed inward toward an axis 136 of the reducing template 130 forcing the sealed pod 131 onto a sharp point 137 of the reservoir access port, which is a seal breaching mechanism. The wall 132 of the sealed pod 131 is pierced, allowing the coating material 103 to leave the reservoir chamber 128. Continued depression of the flexible member 134 collapses the reservoir chamber 128, causing the coating material 103 to flow out of the reservoir chamber 128 through the reservoir access port 133 and into the reducing template 130 where it contacts the medical device 138. Once the coating material 103 is fully dispensed from the reservoir chamber 128, the medical device 138 may be withdrawn in the direction of arrow 135. As the medical device 138 is withdrawn, excess coating material 103 is removed until the medical device 138 completely exits the apparatus 94, at which point the coating is complete and a uniform thickness layer of coating material 103 has been applied to the medical device 138. The medical device 138 may be rotated about the axis 136 of the reducing template 130 while being withdrawn from the apparatus 94 to more evenly distribute the coating material 103. The apparatus 94, may be single use, or the now expended (formerly sealed) pod 131 may be removed and the apparatus 94 cleaned and sterilized for repeat use.

Figure 18:
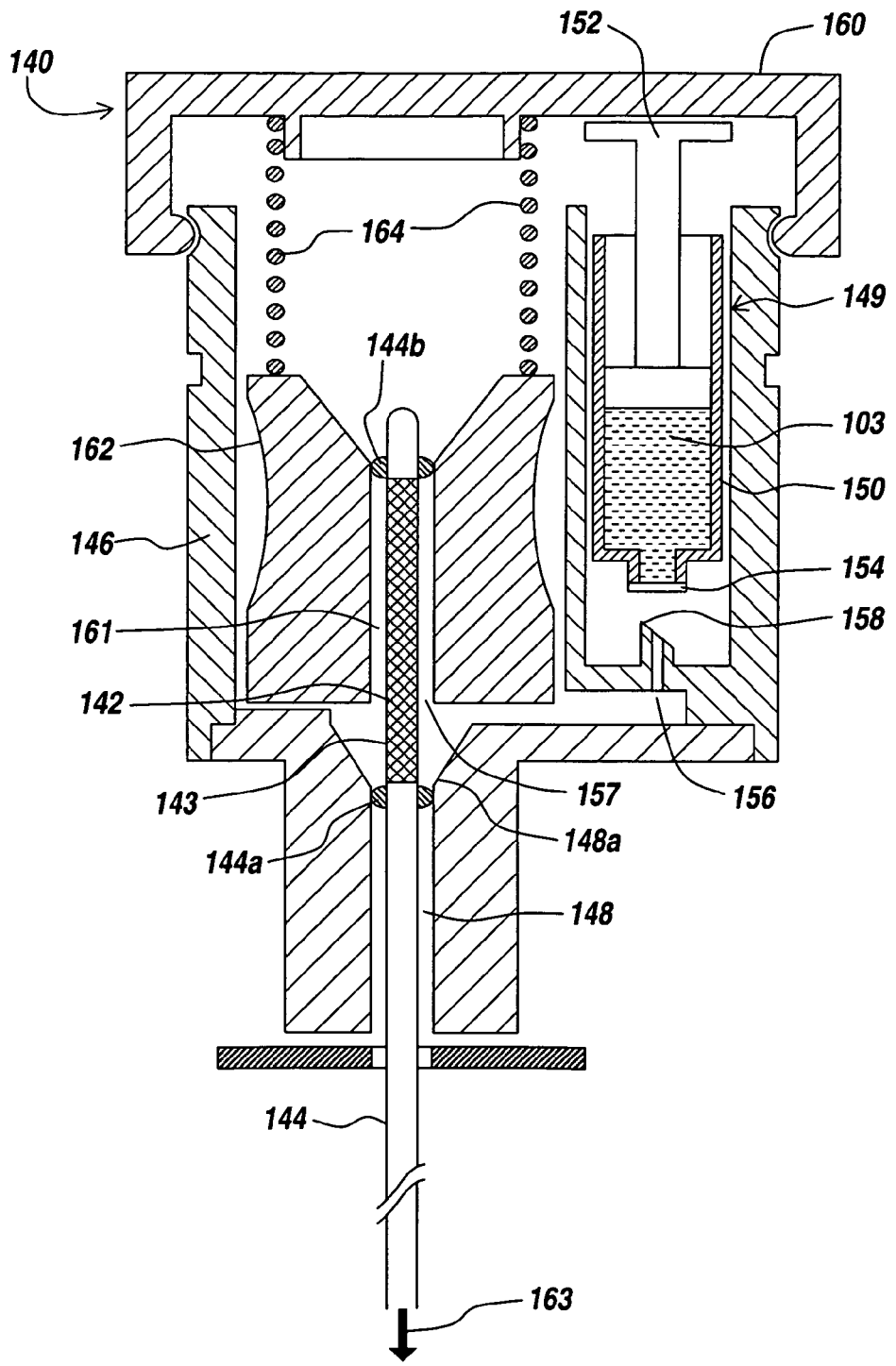
FIG. 18 is a diagrammatic illustration of another apparatus for coating a medical device including a dispenser and a floating piston, in accordance with another embodiment of the present invention.

FIG. 18 illustrates an apparatus 140 for coating a medical device 142 including a housing 146, a dispenser 149 and a floating piston 162, in accordance with another embodiment of the present invention. The dispenser 149 with a sealed reservoir chamber 150 containing coating material 103 can be prepackaged with the apparatus 140, or a detented cap 160 of the apparatus 140 can be removed to load the dispenser 149 into the apparatus 140. The sealed reservoir chamber 150 forms a preserving reservoir for the coating material 103. A septum 154 covers one end of the dispenser 149 to seal that end of the reservoir chamber 150. A plunger 152 seals the reservoir chamber 150 at an opposite end. A medical device 142 in the form of a catheter 144 with a mounted stent 143 is inserted into a reducing template 148 of the apparatus 140 such that a proximal balloon cone 144a of the catheter 144 is positioned at the base of a conic section 148a of the reducing template 148, and a distal balloon cone 144b of the catheter is positioned within a lumen 161 of the floating piston 162. The lumen 161 of the floating piston 162 forms an extension of the reducing template 148. When the detented cap 160 is depressed, a spring 164 is loaded, which loads a floating piston 162 while simultaneously forcing the septum 154 of the preserving reservoir chamber 150 onto a piercing point 158 of a reservoir access lumen, which is a seal breaching mechanism. The septum 154 is pierced before the detented cap 160 is fully depressed. Further depression of the detented cap 160 causes a plunger 152 to push the coating material 103 out of the reservoir chamber 150 of the dispenser 149, through the reservoir access lumen 156, and into a coating cylinder 157, which forms part of the reducing template 148. As the coating material 103 fills the coating cylinder 157, the floating piston 162 is compressed by the coating material 103 against the spring 164. This creates a positive pressure of coating material within the coating cylinder 157, forcing the coating material into all the nooks and crevices of the mounted stent 143. The catheter 144 with the mounted stent 143 is then withdrawn in the direction of arrow 163. The coating material 103 within the coating cylinder 157 is maintained at a positive pressure until the distal balloon cone 144b of the catheter 144 exits the floating piston 162. Excess coating material 103 is removed from the medical device 142 in the reducing template 148 as the medical device 142 is withdrawn until the medical device 142 fully exits the apparatus 140, at which point the coating is complete and a uniform thickness layer of coating material 103 has been applied to the medical device 142.

FIGS. 19A and 19B illustrate an apparatus 164 including a thumb actuated cartridge 186 for coating a medical device, in accordance with another embodiment of the present invention. A catheter 168 with a mounted stent 166 is inserted into a reducing template 172 in a housing 170 of the apparatus 164 and is positioned such that a proximal catheter balloon cone 168a is positioned at a base of the conic 172a of the reducing template 172 and the body of the mounted stent 166 is positioned within a coating chamber 173. A thumb activated cartridge 186 includes a plunger 178 with a plunger seal 178a, a spring 180, and a sealed reservoir chamber 176 containing coating material 103. The reservoir chamber 176 and the septum 188 form a preserving reservoir which contains and optionally preserves the coating material 103. At one end of the reservoir chamber 176, a septum 188 seals and optionally preserves the coating material 103. At the opposite end of the reservoir chamber 176 a plunger seal 178a seals and optionally preserves the coating material 103. The spring 180 is preloaded. The plunger 178 includes two plunger retaining balls 182, which prevent the plunger 178 from moving before the apparatus 164 is activated. One of ordinary skill in the art will appreciate that a plurality of plunger retaining balls 182 beyond those illustrated can be utilized. The apparatus 164 is activated by depressing the thumb activated cartridge 186 in the direction of arrow 191. Depressing the thumb activated cartridge 186 forces the plunger retaining balls 182 past surface protrusions 183, which previously prevented motion of the plunger retaining balls 182. As shown in FIG. 19B, once the plunger retaining balls 182 are past the surface protrusions 183, the thumb activated cartridge 186 moves sufficiently far to drive the septum 188 into a piercer 190, which is a seal breaching mechanism. Additionally, once the plunger retaining balls 182 are past the protrusions 183, the plunger 178 is free to move in the direction specified by arrow 191 under the force of the preloaded spring 180. The plunger 178 pushes the coating material 103 through a hole in the pierced septum 188, through the reservoir access port 184, and into the coating chamber 173. The spring loaded plunger 178 maintains positive pressure in the coating chamber 173, forcing the coating material 103 into all of the nooks and crevices of the mounted stent 166. FIG. 19B depicts the apparatus 164 after the septum 188 has been pierced and about three quarters of the coating material 103 has flowed through the reservoir access port 184 and partially filled the coating chamber 173. After the plunger 178 has moved to the end of the thumb activated cartridge 186, the catheter 168 with a mounted stent 166 is withdrawn from the apparatus 164. As the catheter 168 with mounted stent 166 is withdrawn from the apparatus 164, the coating material 103 remains under positive pressure from the spring loaded plunger 178. Excess coating material 103 is removed by the reducing template 172 as the mounted stent 166 is withdrawn, until the mounted stent 166 completely exits the apparatus 164. After withdrawal, the mounted stent 166 has a uniform thickness layer of coating material 103. It should be noted that the land length of the application reducing template 172 can influence the consistency of the coating weight on the medical device.

Figure 20:
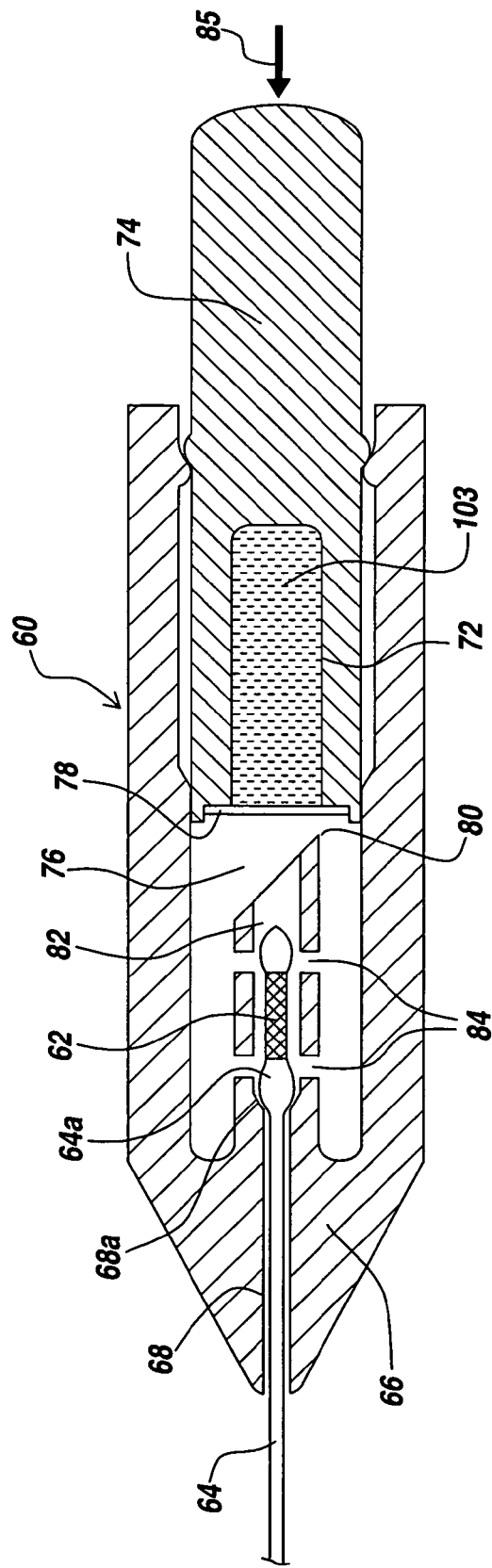
FIG. 20 is a diagrammatic illustration of another apparatus for coating a medical device including a reservoir containing section, in accordance with another embodiment of the present invention.

FIG. 20 illustrates an apparatus 60 for coating a medical device 62 in accordance with another embodiment of the present invention. The apparatus 60 includes a reservoir containing section 74 which includes a sealed reservoir chamber 72 containing coating material 103 capped with a rupture membrane 78 that contains and optionally preserves the coating material. The reservoir chamber 72 and the rupture membrane 78 form a preserving reservoir. The housing 66 of the apparatus 60 includes a reducing template 68, a coating chamber 82, flow channels 84, a reservoir access port 76, and a sharp point 80 of the coating chamber, which is a seal breaching mechanism. A medical device 62 mounted on a catheter 64 is inserted into the reducing template 68 of the apparatus 60 such that the proximal balloon cone 64a of the catheter is positioned at the base of the conical section 68a of the reducing template 68 and the medical device 62 is positioned within the coating chamber 82. To activate the apparatus 60, the reservoir containing section 74 is depressed in the direction of arrow 85. When the reservoir containing section 74 moves in the direction of arrow 85, the rupture membrane 78 is driven into the sharp point 80 of the coating chamber which pierces the rupture membrane 78. As the reservoir containing section 74 is further depressed, the reservoir chamber 72 is driven over the open ended coating chamber 82 and fills the coating chamber 82 and the medical device 62 contained therein with coating material 103. While the catheter 64 with a mounted medical device 62 is withdrawn from the apparatus 60, the reducing template 68 removes excess coating material 103. After removal, a complete and uniform thickness layer of coating material 103 has been applied to the medical device 62.

Figure 21:
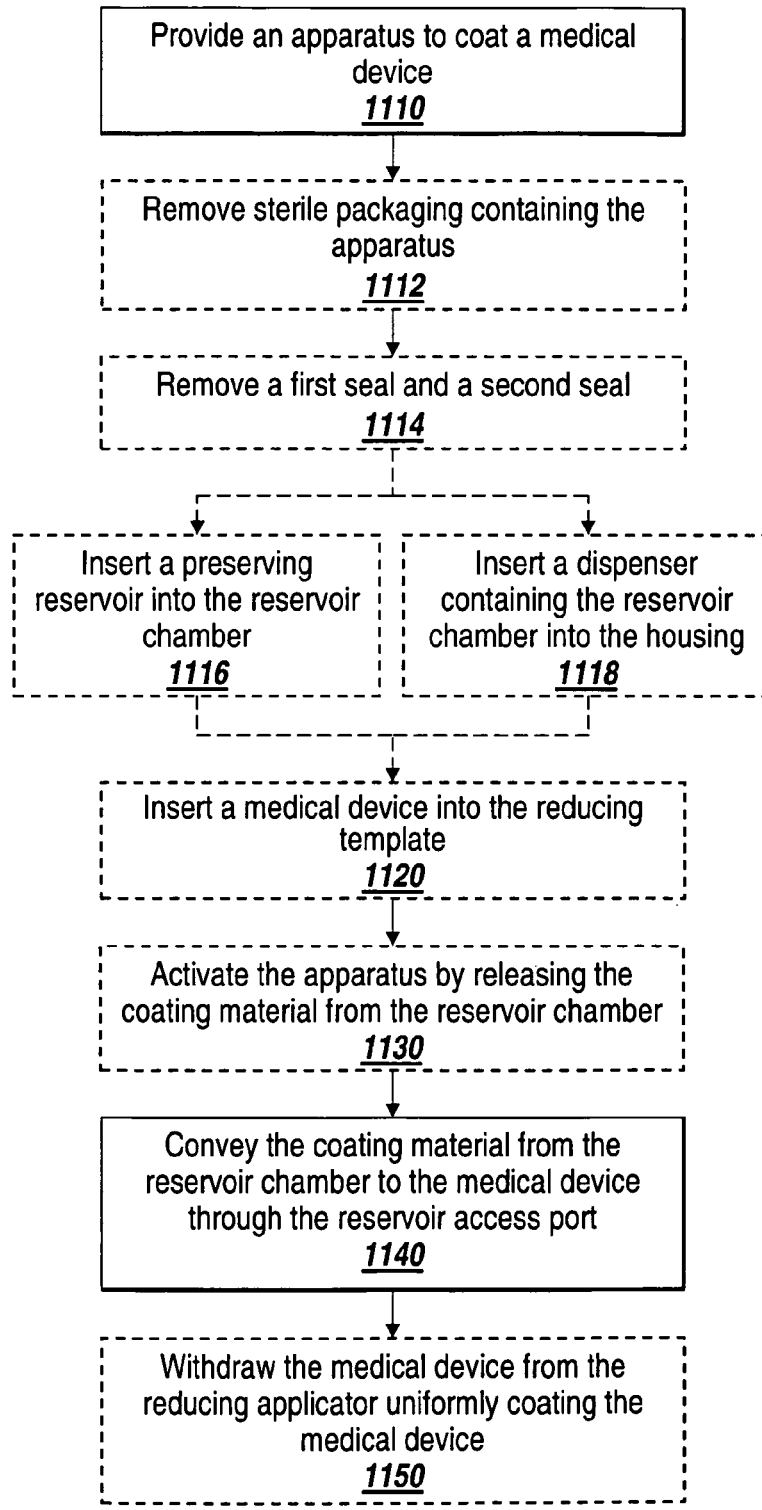
FIG. 21 is a flow chart illustrating a method of coating a medical device using the apparatus depicted in FIG. 15, in accordance with one embodiment of the present invention.

FIG. 21 is a flowchart illustrating another example implementation of the method of FIG. 4 using the apparatus shown in FIG. 15. In accordance with the steps illustrated in FIG. 21, an apparatus 90 to coat a medical device is provided (step 1110). The apparatus 90 includes a housing 102, a reservoir chamber 104 disposed in the housing 102 adapted to contain a coating material 103, a seal breaching mechanism in the form of a sharp point 107 of the reservoir access port, and a reducing template 105 disposed in the housing 102 and sized to receive the medical device therethrough for application of the coating material 103. The apparatus 90 further includes a reservoir access port 106 disposed in the housing 102 adapted to fluidly couple the reducing template 105 with the reservoir chamber 104 upon activation of the apparatus 90 for coating the medical device. According to aspects of the illustrative embodiment, the medical device may be inserted into the reducing template 105 before the apparatus is activated (step 1120). The coating apparatus 90 may be activated by releasing the coating material 103 from the sealed reservoir chamber 104 (step 1130). Releasing the coating material 103 from the sealed reservoir chamber may include breaching the sealed reservoir chamber 104 using the sharp point 107 of the reservoir access port. The coating material 103 is conveyed from the reservoir chamber 104 to the medical device though the reservoir access port 106 (step 1140). The medical device may be withdrawn from the reducing template 105 uniformly coating the medical device (step 1150). The medical device may be rotated relative to the reducing template 105 about an axis along the reducing template while being withdrawn.

According to further aspects of the illustrative embodiment a preserving reservoir that contains and optionally preserves the coating material may be inserted into the housing (step 1116). Alternately, a dispenser containing the reservoir chamber may be inserted into the housing (step 1118). The reservoir chamber 104 of coating material 103 may be disposed within a dispenser 109 disposed in the housing 102. The volume of the reservoir chamber 104 may be sized to contain a volume of coating material 103 at least sufficient to coat one medical device.

According to aspects of the present invention the preserving reservoir may include a sealed pod containing the coating material. The coating material may include a bio-absorbable liquid. The coating material may further include at least one therapeutic agent. The housing 102 may further include a grip 115. The first end of the reducing template 105 may be flared or may be necked down and may have a cross-sectional area greater than or less than a cross-sectional area of at least a remaining portion of the reducing template. The reducing template 105 is sized and dimensioned to fit over the medical device providing a clearance between an inner wall of the reducing template and the medical device for receiving the coating material 103 for application of the coating material 103 to the medical device. The step of inserting the medical device into the reducing template 105 may distribute coating material 103 along the medical device. The coating material may include an oil containing at least one form of lipid, at least one form of essential fatty acid and/or a partially cured oil The sealed pod may be formed of a wall including a soft non-liquid layer of gelatin and/or a soft non-liquid layer of cellulose. The medical device may include a stent, a catheter and/or a balloon.

According to other aspects of the present invention sterile packaging containing the apparatus may be removed (step 1112). The first seal 113 and second seal 114 may be removed from the reducing template (step 1114).

Figure 22:
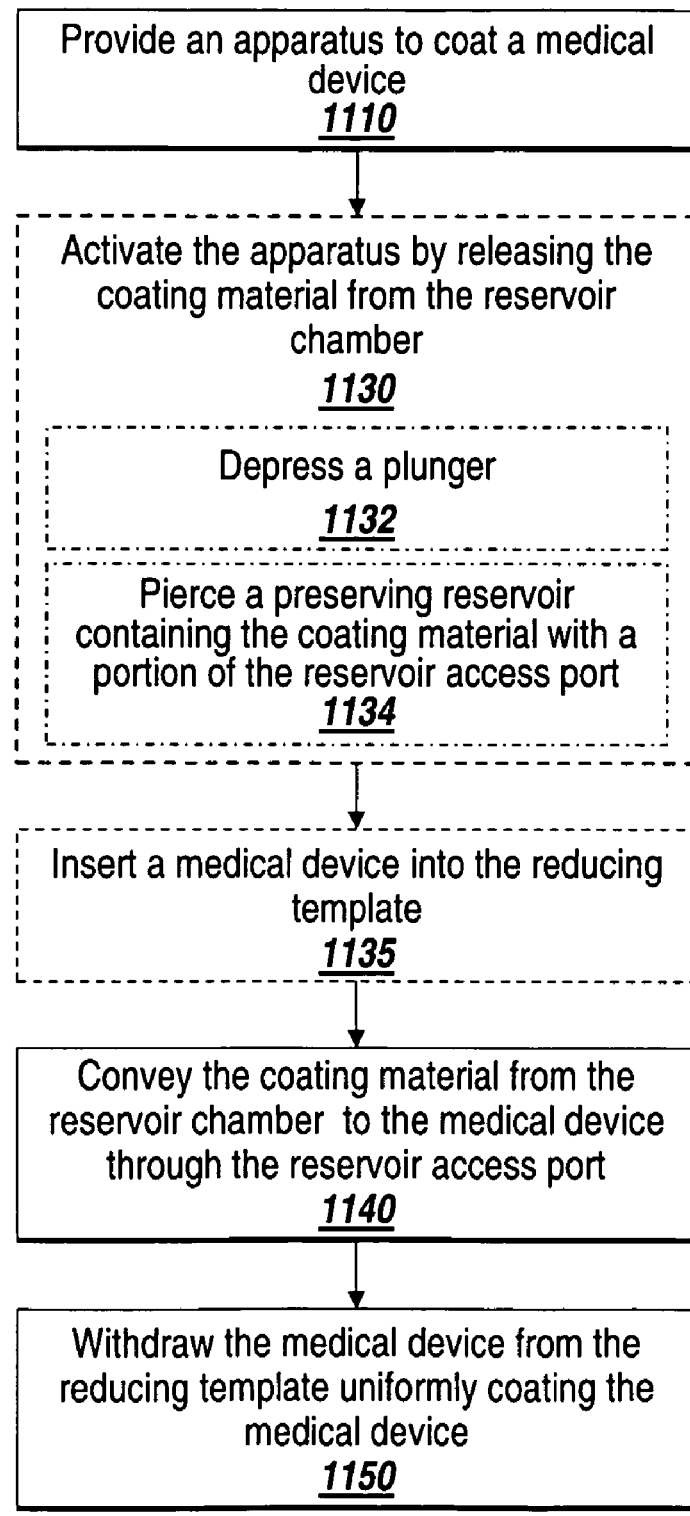
FIG. 22 is a flow chart illustrating a variation of the method of coating a medical device according to aspects of the present invention.

FIG. 22 is a flowchart illustrating possible variations of steps 1130-1140 of FIG. 21. The step of activating the coating apparatus by releasing the coating material 103 from the reservoir chamber 104 (step 1130) may include depressing a plunger 110 (step 1132). Step 1130 may include piercing the septum 111 and the reservoir 104 with a sharp point 107 of the reservoir access port 106 (step 1134). A medical device may be inserted into the reducing template after the apparatus is activated (step 1135).

In the embodiments of the present invention represented in FIGS. 15-22, after activation, the coating material is in the reducing template. The coating material can spread itself substantially throughout the reducing template. The coating material may be spread throughout the reducing template by gravity dependent fluid flow, or by capillary and mechanical/fluidic forces created as the medical device is withdrawn through the reducing template. Additionally, the insertion of the medical device can distribute the coating material throughout the reducing template. The shape and diameter of the reducing template ensures that the medical device will be uniformly coated. The thickness and uniformity of the coating on the medical device is determined by the shape and surface properties of the apparatus, the shape and surface properties of the medical device and the materials properties of the coating material. For a particular reducing template shape formed of a particular material, a particular medical device shape formed of another particular material and a particular coating material, the diameter of the reducing template is chosen relative to the diameter of the medical device based on the desired coating thickness. The clearance, in this case the difference between an inner diameter of the reducing template and an outer diameter of the medical device, the land length of the reducing template, and the rheology of the coating material determines the thickness and the uniformity of the coating. Coatings produced by the apparatus are predictable and repeatable as the amount of coating material in the reducing template is controlled by the size of the reservoir and the structure of the reducing template ensures a repeatable uniform coating of a consistent thickness.

It should be noted that the sealed receptacle, sealed pod, sealed reservoir chamber, and the like, as referenced throughout the present description, include both chambers, receptacles, pods, etc. with actual seals, as well as fully enclosed structures that are substantially impervious to the surrounding environment in terms of preserving or storing the coating material therein. As such, when the present description refers to unsealing, breaking the seal, removing the seal, or the like, such references include any method of penetrating the wall of the receptacle so as to allow the coating material to come into contact with the environment external to the receptacle, chamber, pod, etc., to the extent possible given the particular structure of the apparatus of the embodiment. One of ordinary skill in the art will appreciate that the present invention is not limited to requiring an actual seal placed on to a receptacle, chamber, reservoir, and the like, if it is not necessary to be limited in such a manner for the operation of the embodiment. While the various embodiments of the present invention make reference to each of these structures individually, equivalents of such structures will be apparent to those of ordinary skill in the art, and are intended to be anticipated by the present invention.

The figures herein illustrate some representative embodiments of the apparatus of the present invention. The various elements of the apparatus (ie. medical device, sealed reservoir chamber, reducing template, seals, sleeve, seal breaching mechanism, catheter, catheter cap, stylet, crimp seal, end cap, etc.) may be combined in combinations that are within the scope of the present invention, but are not specifically depicted in this specification due to the practical impossibility of depicting all possible combinations. In addition, the embodiments illustrated, and equivalents thereof, can be incorporated into a kit for providing a coated medical device. The kit primarily incorporating the apparatus of the present invention as described herein, in addition to instructions for use, as would be understood by those of ordinary skill in the art.

The coating apparatus may be used to produce multilayer coatings. After a medical device has been coated using the apparatus, the medical device may be inserted into a different apparatus that contains a reservoir of the same coating material or of a different coating material. This results in a medical device with either two coating layers of the same material or two coating layers of different materials. A third coating apparatus could be used to apply a third coating layer to the medical device that already has two coating layers, and so on. After the application of a coating layer, that layer may be partially or fully cured before the application of the next coating layer. If the diameter of the medical device including coating layers changes significantly during application of the layers, the newest layers may be applied with an apparatus whose reducing template has a larger cross-sectional diameter to accommodate the increasing diameter of the medical device including coating layers. If the additional layers are of the same coating material as the first layer, the multiple coatings may be applied using the same apparatus refilled with a new reservoir for each layer.

It has been previously mentioned that curing of substances such as fish oil can reduce or eliminate some of the therapeutic benefits of the omega-3 fatty acids, including anti-inflammatory properties and healing properties. However, if the coating contains the bio-absorbable carrier component formed of the oil having the therapeutic benefits, the pre-treatment can be cured to better adhere the pre-treatment to the stent, without losing all of the therapeutic benefits resident in the pre-treatment, or in the subsequently applied coating. Furthermore, the cured pre-treatment provides better adhesion for the coating relative to when the coating is applied directly to the stent surface. In addition, the pre-treatment, despite being cured, remains bio-absorbable, like the coating.

The pre-treatment 22 can be applied to both the interior surface 16 and the exterior surface 18 of the stent 10, if desired, or to one or the other of the interior surface 16 and the exterior surface 18. Furthermore, the pre-treatment 22 can be applied to only portions of the surfaces 16 and 18, or to the entire surface, if desired.

The application of the coating to the medical device can take place in a manufacturing-type facility and subsequently shipped and/or stored for later use. Alternatively, the coating can be applied to the medical device just prior to implantation in the patient. The process utilized to prepare the medical device will vary according to the particular embodiment desired. In the case of the coating being applied in a manufacturing-type facility, the medical device is provided with the coating and subsequently sterilized in accordance with any of the methods provided herein, and/or any equivalents. The medical device is then packaged in a sterile environment and shipped or stored for later use. When use of the medical device is desired, the medical device is removed from the packaging and implanted in accordance with its specific design.

In the instance of the coating being applied just prior to implantation, the medical device can be prepared in advance. The medical device, for example, can be sterilized and packaged in a sterile environment for later use. When use of the medical device is desired, the medical device is removed from the packaging, and the coating substance is applied to result in the coating resident on the medical device.

The present invention provides methods and devices for applying a coating to medical devices such as a stent. The methods and devices of the present invention provide a means for applying a coating that provides improved uniformity and coverage in a repeatable and controlled manner shortly before use of the implant. The methods and devices also provide increased consistency in coating from device to device. This in turn allows for greater control of dosage of the bio-absorbable carrier and therapeutic agent.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

What is claimed is:

1. An apparatus for coating a medical device comprising:
    a housing;
    a sealed reservoir chamber disposed in the housing, the reservoir chamber containing a coating material in a sealed manner;
    a reducing template disposed in the housing, the reducing template having a first end and a second end, and sized to receive the medical device therethrough for application of the coating material; and
    a reservoir access port disposed in the housing and adapted to fluidly couple the reducing template with the reservoir chamber upon activation of the apparatus for coating the medical device;
    wherein the second end of the reducing template is open and is sized and dimensioned to enable removal of excess coating material from the medical device upon removal of the medical device through the second end.

2. The apparatus of claim 1, wherein the reservoir chamber forms a preserving reservoir.

3. The apparatus of claim 1, wherein the reservoir chamber contains a preserving reservoir.

4. The apparatus of claim 3, wherein the preserving reservoir comprises a sealed pod containing the coating material.

5. The apparatus of claim 3, wherein the preserving reservoir is formed of a reservoir wall comprised of a soft non-liquid layer of gelatin or cellulose.

6. The apparatus of claim 1, wherein the coating material comprises a bio-absorbable liquid.

7. The apparatus of claim 1, wherein the coating material comprises a bio-absorbable liquid and at least one therapeutic agent.

8. The apparatus of claim 1, wherein the first end of the reducing template is flared and has a cross-sectional area greater than a cross-sectional area of at least a remaining portion of the reducing template.

9. The apparatus of claim 1, wherein the first end of the reducing template is necked down and has a cross-sectional area less than a cross-sectional area of at least a remaining portion of the reducing template.

10. The apparatus of claim 1, wherein the first end of the reducing template has a land that is dimensioned to deposit a consistent coating weight or thickness on a device.

11. The apparatus of claim 1, wherein the reducing template is sized and dimensioned to fit over the medical device providing a clearance between an inner wall of the reducing template and the medical device for receiving the coating material for application of the coating material to the medical device.

12. The apparatus of claim 1, wherein the reducing template is expandable to fit over the medical device providing a clearance between an inner wall of the reducing template and the medical device for receiving the coating material for application of the coating material to the medical device.

13. The apparatus of claim 1, wherein the reducing template is expandable to fit over the medical device contacting the medical device while still leaving a nominal clearance between an inner wall of the reducing template and the medical device for receiving the coating material for application of the coating material to the medical device.

14. The apparatus of claim 1, wherein the reservoir access port has a first end and a second end, the second end of the reservoir access port having at least one sharp point adapted to puncture a preserving reservoir included in the apparatus containing the coating material.

15. The apparatus of claim 1, further comprising a plunger disposed in the housing adjacent to the reservoir chamber and adapted to apply a compression force to the coating material to move the coating material in the direction of the reservoir access port when depressed.

16. The apparatus of claim 1, wherein the reservoir chamber is disposed within a dispenser disposed in the housing.

17. The apparatus of claim 1, further comprising a first seal and a second seal, wherein the first seal seals a first end of the reducing template and the second seal seals a second end of the reducing template and wherein the first seal and second seal are adapted to maintain the sterile integrity of an interior of the reducing template.

18. The apparatus of claim 1, wherein the volume of the reservoir chamber is sized to contain a volume of coating material at least sufficient to coat one medical device.

19. The apparatus of claim 1, wherein the housing further comprises a grip for holding the housing during use.

20. The apparatus of claim 1, wherein the coating material comprises an oil containing at least one form of lipid, at least one form of essential fatty acid, or both.

21. The apparatus of claim 1, wherein the coating material comprises a partially cured oil.

22. The apparatus of claim 1, wherein the medical device comprises a stent, a catheter, or a balloon.

23. The apparatus of claim 1, further comprising a seal breaching mechanism disposed in the housing and adapted to breach the sealed reservoir chamber upon activation of the apparatus.

24. A kit for coating a medical device comprising:
a coating material;
a dispenser comprising:
- a housing;
- a sealed reservoir chamber containing the coating material;
- a reducing template disposed in the housing, the reducing template having a first end and a second end, and sized to receive the medical device therethrough for application of the coating material; and
- a reservoir access port disposed in the housing and adapted to fluidly couple the reducing template with the reservoir chamber upon activation of the apparatus; the medical device; and instructions for use;
wherein the second end of the reducing template is open and is sized and dimensioned to enable removal of excess coating material from the medical device upon removal of the medical device through the second end.

25. The kit of claim 24, wherein the reservoir chamber forms a preserving reservoir.

26. The kit of claim 24, wherein the reservoir chamber contains a preserving reservoir.

27. The kit of claim 26 wherein the preserving reservoir comprises a sealed pod containing the coating material.

28. The kit of claim 26, wherein the preserving reservoir is formed of a reservoir wall comprised of a soft non-liquid layer of gelatin or cellulose.

29. The kit of claim 24, wherein the coating material comprises a bio-absorbable liquid.

30. The kit of claim 24, wherein the coating material comprises a bio-absorbable liquid and at least one therapeutic agent.

31. The kit of claim 24, wherein the first end of the reducing template is flared and has a cross-sectional area greater than a cross-sectional area of at least a remaining portion of the reducing template.

32. The kit of claim 24, wherein the first end of the reducing template is necked down and has a cross-sectional area less than a cross-sectional area of at least a remaining portion of the reducing template.

33. The kit of claim 24, wherein the first end of the reducing template has a land that is dimensioned to deposit a consistent coating weight on a device.

34. The kit of claim 24, wherein the reducing template is sized and dimensioned to fit over the medical device providing a clearance between an inner wall of the reducing template and the medical device for receiving the coating material for application of the coating material to the medical device.

35. The kit of claim 24, wherein the reducing template is expandable to fit over the medical device providing a clearance between an inner wall of the reducing template and the medical device for receiving the coating material for application of the coating material to the medical device.

36. The kit of claim 24, wherein the reducing template is expandable to fit over the medical device contacting the medical device while still leaving a nominal clearance between an inner wall of the reducing template and the medical device for receiving the coating material for application of the coating material to the medical device.

37. The kit of claim 24, wherein the reservoir access port has a first end and a second end, the second end of the reservoir access port having at least one sharp point adapted to puncture a preserving reservoir included in the dispenser containing the coating material.

38. The kit of claim 24, further comprising a plunger disposed in the housing adjacent to the reservoir chamber and adapted to apply a compression force to the coating material to move the coating material in the reservoir chamber in the direction of the reservoir access port when depressed.

39. The kit of claim 24, wherein the reservoir chamber containing coating material is disposed within a dispenser disposed in the housing.

40. The kit of claim 24, further comprising a first seal and a second seal, wherein the first seal seals a first end of the reducing template and the second seal seals a second end of the reducing template and wherein the first seal and the and second seal are adapted to maintain the sterile integrity of an interior of the reducing template.

41. The kit of claim 24, wherein the volume of the reservoir chamber is sized to contain a volume of coating material at least sufficient to coat one medical device.

42. The kit of claim 24, wherein the coating material comprises an oil containing at least one form, of lipid, at least one form of essential fatty acid, or both.

43. The kit of claim 24, wherein the coating material comprises a partially cured oil.

44. The kit of claim 24, wherein the medical device comprises a stent, a catheter, or a balloon.

45. The kit of claim 24, further comprising a seal breaching mechanism disposed in the housing and adapted to breach the sealed reservoir chamber upon activation of the apparatus.

\* \* \* \* \*